United States Patent [19]

Valcke et al.

[11] Patent Number: 5,733,259

[45] Date of Patent: Mar. 31, 1998

[54] METHOD AND APPARATUS FOR CLOSED LOOP DRUG DELIVERY

[75] Inventors: Christian P. Valcke, Los Angeles; Walter J. Bochenko, Encinitas; Robert S. Hillman, San Diego, all of Calif.

[73] Assignee: Gensia Pharmaceuticals, Inc., San Diego, Calif.

[21] Appl. No.: 363,863

[22] Filed: Dec. 22, 1994

Related U.S. Application Data

[63] Continuation of Ser. No. 830,304, Jan. 31, 1992, abandoned.

[51] Int. Cl.$^6$ ................................................. A61M 5/00
[52] U.S. Cl. ............................... 604/66; 128/DIG. 12; 128/DIG. 13
[58] Field of Search ................ 604/65–67; 128/DIG. 12, 128/DIG. 13

[56] References Cited

U.S. PATENT DOCUMENTS

| | | |
|---|---|---|
| 2,690,178 | 9/1954 | Bickford . |
| 3,946,731 | 3/1976 | Lichtenstein . |
| 4,055,175 | 10/1977 | Clemens . |
| 4,078,562 | 3/1978 | Friedman . |
| 4,080,966 | 3/1978 | McNally . |
| 4,127,121 | 11/1978 | Westenskau . |
| 4,180,074 | 12/1979 | Murry . |
| 4,211,239 | 7/1980 | Raemer . |
| 4,280,494 | 7/1981 | Cosgrcue . |
| 4,291,692 | 9/1981 | Bauman . |
| 4,300,572 | 11/1981 | Knighton . |
| 4,392,849 | 7/1983 | Petre . |
| 4,457,751 | 7/1984 | Rodler ................................. 604/66 |
| 4,533,346 | 8/1985 | Cosgrove . |
| 4,551,133 | 11/1985 | Zegers De Beyl et al. ........... 604/66 |
| 4,710,164 | 12/1987 | Levin et al. ........................... 604/66 |
| 4,718,891 | 1/1988 | Lipps ................................. 604/31 |
| 4,722,726 | 2/1988 | Sanderson . |
| 4,871,351 | 10/1989 | Feingold ............................. 604/66 |
| 5,088,978 | 2/1992 | Hillman et al. ...................... 604/20 |
| 5,108,363 | 4/1992 | Tuttle et al. ......................... 604/20 |

OTHER PUBLICATIONS

Voss, Gregory I, et al, "Adaptive Multivariable Drug Delivery: Control of Arterial Pressure and Cardiac Output in Anesthetized Dogs", IEEE Transactions on Biomedical Engineering, vol. BME–34, No. 8, Aug., 1987.

Frucht, et al, "Rechnergestutzte Blutdruckregelung durch kreislaufwirksame Medikamente", pp. 333–337, (1986), Anasth, Intensivther, Notfalimed, 21 (Translation attached).

Poon, Chi–Sang, "Estimation of Response Curves in Closed–Loop Physiological Control", pp. 1481–1491, (1986), J.Appl.Physiol. 61(4).

Kenny, G.N.C. et al, "Computer Control of an Imed 929 Infusion Pump", pp. 227–228 (Journal Unknown).

(List continued on next page.)

Primary Examiner—Michael Buiz
Assistant Examiner—Nancy Mulcare
Attorney, Agent, or Firm—Lyon & Lyon LLP

[57] ABSTRACT

A closed-loop drug delivery system uses patient response and rule based decision making methods to achieve operator specified responses for diagnostic purposes. In the preferred embodiment, cardiac diagnosis is performed by pharmacologically stressing the heart by administration of an exercise simulating agent drug. In the preferred method, a protocol is defined, which preferably includes a target for a physiologic variable, such as heart rate, and a plan to achieve that target value. Preferably, the plan includes a specification of the desired rate of increase in that variable, such as the rate of increase in the heart rate per minute. The plan comprises the desired changes in the physiologic variable as a function of time. While any desired function may be used, the more common modes include RAMP, HOLD, LEVEL and TARGET mode. In one aspect of this invention, the protocol may be varied by the operator after drug administration has begun. Further, in one embodiment, the protocol includes a definition of an acceptable zone of deviation from the plan, such that if the patient physiologic variable deviates from the permissible zone, alternate control rules are implemented. Preferably, saturation detection and avoidance is implemented.

51 Claims, 11 Drawing Sheets

OTHER PUBLICATIONS

*Ritchie, R. Gilbert et al*, "Closed–Loop Control of an Anesthesia Delivery System: Development and Animal Testing", pp. 437–443, (Jun. 1987), IEEE Transactions on Biomedical Engineering, vol. BME–34, No. 6.

*Jannett, Thomas C. et al*, "Modeling the Rate of Premature Ventricular Contractions and its Response to Lidocaine Infusion", pp. 636–641, (Aug. 1987), IEEE Transactions on Biomedical Engineering, vol. BME–34, No. 8.

*Childress, Dudley S.*, "Closed–Loop Control in Prosthetic Systems: Historical Perspective", pp. 293–303, (1980), Annals of Biomedical Engineering, vol. 8.

*Noordergraaf, Abraham*, "The Development of Recognition of Component Significance in Closed–Loop Cardiovascular Control", pp. 391–403, (1980), Annals of Biomedical Engineering, vol. 8.

Sagawa, Kiichi, "Closed–Loop Physiological Control of the Heart", pp. 415–429, (1980), Annals of Biomedical Engineering, vol. 8.

*Rekate, Harold L.*, "Closed–Loop Control of Intracranial Pressure", pp. 515–522, (1980), Annals of Biomedical Engineering, vol. 8.

*Ritchie, R.G. et al*, "Integrated Closed–Loop Control of an Anesthesia Delivery System: Development and Animal Testing", p. 125, Abstracts.

*Collins, Steve M. et al*, "Computer Control of Cardiac Arrhythmia", pp. 276–279, (1979), IEEE, Session 13.

*Northrop, Robert B. et al*, "Closed–Loop, Microprocessor Control of Drug Injection by Integral Pulse Frequency Modulation", pp. 33–36, (1985), IEEE.

*Tuteur, Franz B. et al*, "Closed–Loop Identification of Hemodynamic Control Systems", p. 38, Abstracts.

*Spencer, W.J.*, "A Review of Programmed Insulin Delivery Systems", pp. 237–251, (Mar. 1981), IEEE Transactions on Biomedical Engineering, vol. BME–28, No. 3.

*Wilkins, Ebtisam et al*, "Biomaterials for Implanted Closed Loop Insulin Delivery System: A Review", pp. 167–213, (1990), Biosensors and Bioelectronics 5.

*Woodruff, Eileen A. et al*, "Closed–Loop Regulation of a Physiological Parameter by an IPFM/SDC (Integral Pulse Frequency Modulated/Smith Delay Compensator) Controller)", pp. 595–602, (Aug. 1987), IEEE Transactions on Biomedical Engineering, vol. BME–34, No. 8.

*Packer, John S. et al*, "An Adaptive Controller for Closed–Loop Management of Blood Pressure in Seriously Ill Patients", pp. 612–616, (Aug. 1987), IEEE Transactions on Biomedical Engineering, vol. BME–34, No. 8.

*Slate, J.B. et al*, "A Model for Design of a Blood Pressure Controller for Hypertensive Patients", pp. 285–289, (1979), IEEE.

"The Automatic Control of Blood Pressure", pp. 460–466.

*Voss, Gregory I, et al*, "Automated Drug Delivery Systems: Use of Control Systems to Improve Patient Therapy".

Jannett, T.C. et al, "Modeling the Rate of Premature Ventricular Contractions and its Response to Lidocaine Infusion", pp. 636–641, (Aug. 1987), IEEE Transactions on Biomedical Engineering, vol. BME–34, No. 8.

*Johnson, Craig L. et al*, "Adaptive Feedback Control of Blood Pressure: Model–Based Design and Testing", (Apr. 6–8, 1988), IFAC Symposium on Modelling and Control in Biomedical Systems, Venice, Italy.

*Jannett, T.C. et al*, "Modeling and Closed–Loop Lidocaine Infusion for Control of Ventricular Arrhythmia".

*Jannett, T.C. et al*, "Modeling and Closed–Loop Pharmacologic control of the Ventricular Response Rate During Induced Atrial Fibrilation in Anesthetized Dogs".

METHOD AND APPARATUS FOR CLOSED LOOP DRUG DELIVERY

CROSS-REFERENCE TO RELATED APPLICATIONS

This is a continuation of application Ser. No. 07/830,304, filed on Jan. 31, 1992 now abandoned and which designated in the U.S.

This application is related to U.S. Ser. No. 308,683, 5,108,683 filed Feb. 9, 1989, which is a continuation-in-part of U.S. Ser. No. 157,875, filed Feb. 19, 1988, the disclosures of which are incorporated herein by reference.

FIELD OF THE INVENTION

The invention relates generally to a closed loop drug delivery system using a rule based administration method. More particularly, the invention relates to methods and apparatus for use in the administration of an exercise simulating agent ("ESA") which elicits a cardiovascular response similar to that resulting from aerobic activity. This apparatus and method is used advantageously in the diagnosis, evaluation and treatment of coronary artery disease, by providing for closed loop drug delivery to generate a cardiac stress related response.

BACKGROUND AND INTRODUCTION TO THE INVENTION

Heart disease is the number one killer in the United States and a leading cause of death worldwide. Currently, heart disease, stroke and related disorders account for nearly one million deaths per year in the United States, almost as many deaths as from all other causes combined. Cardiovascular and cerebrovascular diseases affects approximately 65 million people in the United States, roughly one out of every four. Approximately 5 million people in the United States suffer from coronary artery disease ("CAD"), resulting in over 1.5 million heart attacks yearly, of which over 500,000 are fatal. The annual economic cost of cardiovascular disease alone is estimated to be 85 billion dollars.

Atherosclerosis is the most common form of arteriosclerosis, commonly referred to as 'hardening of the arteries'. Atherosclerosis is a degenerative process that narrows or blocks arteries in the heart, brain and other parts of the body. The interior walls become lined with deposits of fat, cholesterol, fibrin, cellular waste products and calcium. These deposits form a rough, thick surface inside the blood vessels and interfere with both the smooth flow of blood and the amount of blood carried through the arteries. This narrowing of the blood vessels restricts blood flow, causing ischemia (deficiency of blood at the heart tissue due to either functional constrictions or obstructions of a blood vessel), and is the underlying pathologic condition in many forms of cardiovascular disease including CAD, aortic aneurysm, peripheral vascular disease and stroke.

In the majority of cases, the first indication of atherosclerosis is seen during exercise when the oxygen requirement of the heart muscle (myocardium) increases. Indeed, atherosclerosis is generally silent until it manifests itself as CAD, peripheral vascular disease, stroke or sudden death.

Disorders of the coronary arteries are common manifestations of atherosclerosis. CAD develops when the coronary circulation is insufficient to supply the oxygen requirements of the heart muscle, resulting in ischemia. CAD has three major clinical manifestations: angina pectoris, a condition marked by periodic episodes of chest pain, especially during exertion, that result from transient and reversible myocardial ischemia (when CAD has progressed such that it is clinically apparent, it is also referred to as ischemic heart disease); myocardial infarction, the term used to describe acute necrotic changes in the myocardium that are usually secondary to coronary occlusion (heart attacks); and sudden death, an unexpected cardiac death occurring within an hour of the onset of the heart attack, often without symptoms.

Diagnosis and evaluation of coronary artery disease is challenging to the practicing physician because myocardial ischemia occurs at irregular intervals or without pain or other symptoms. Historically, the diagnosis and management of coronary artery disease has been performed using both non-invasive and invasive procedures. Prior to 1970, the principal non-invasive techniques available for the evaluation of the patient with heart disease were a clinical examination, chest x-ray and electrocardiograph ("ECG"). If these various modalities were inadequate and clinical symptoms were present, patients were often subject to invasive techniques of cardiac catheterization, selective angiography, or both, with the resultant discomfort, risk and necessity for hospitalization. More recently, the most common non-invasive diagnostic procedure is the resting ECG. An ECG is performed with the patient at rest, and is useful for diagnosing cardiovascular disease states such arrhythmias, hypertrophy (enlargement of the heart), and evidence of an evolving or prior heart attack. However, this test is generally not sufficiently sensitive to detect coronary disease in its early stages. More recently, echocardiography and radionuclide imaging have been used for non-invasive diagnostic purposes. Echocardiography employs ultrasound to create an image of the heart, producing real time images of anatomical structures and heart wall motion. Radionuclide imaging uses radioactive agents and specialized camera equipment to create an image of the heart. Once injected into the blood stream, radionuclide imaging agents such as thallium are taken up rapidly by healthy cardiac tissue, while poorly profused tissues take up less of the tracer. Areas with less of the imaging agent indicate the presence of occluded coronary arteries or dead tissue.

While each of the primary noninvasive diagnostic techniques of ECG, echocardiography and radionuclide imaging may be performed with the patient at rest, their diagnostic value is enhanced by stressing the patients heart. Exercise increases the heart's need for oxygen, causing healthy coronary arteries to become dilated and blood flow through these vessels to increase. Occluded arteries impede blood flow and may not accommodate the increased needs of the heart, causing ischemia. Ischemia may elicit a symptomatic response, e.g., chest pain, or may cause cardiac disfunction, e.g., abnormal heart wall motion, which can often be diagnosed by these non-invasive methods.

Currently, the most common exercise stress testing is performed with ECG monitoring. Typically, exercise stress testing is performed after a baseline resting ECG is taken. A patient is then closely monitored through a protocol of sequential levels of exercise. The Bruce protocol is the most common protocol used in the United States. It specifies the speed and level of the incline of a motor driven tread mill during a total of seven 3-minute exercise states with no rest periods. The test is stopped when any of the following occur: when the protocol is completed; when the patient reaches a pre-set heart rate goal; when the patient experiences acute discomfort; when a diagnostic change occurs in the ECG or blood pressure; or when the patient fatigues.

Despite the fact that exercise stress testing is an important method for the diagnosis of coronary artery disease, there are numerous drawbacks which limit its overall usage. A significant problem with the procedure is that exercise must be maximal in order to obtain the greatest sensitivity. In other words, for a test to be considered diagnostically revealing, either the patient must reach a level of stress that causes ischemia or the patient must complete the protocol by reaching a predetermined maximal heart rate.

The first group of patients with whom exercise stress testing cannot be used are those who are physically unable to exercise. Approximately 20–30% of the relevant subject population fall in this category. Often, patients cannot exercise due to any number of causes, such as, arthritis, limb abnormalities, obesity, obstructive lung disease, peripheral vascular disease or other disfunction.

The second major class of patients incompatible with exercise stress testing are those for whom the results are inconclusive due to an inability to achieve the necessary heart rate. Again, this comprises from 20–30% of the subject patients.

Thirdly, exercise stress testing involving physical motion is generally incompatible with echocardiography and radionuclide imaging. With echocardiography, lung expansion and patient movement reduces the quality of the echocardiography ultrasound image. With radionuclide imaging, the image cannot be made at the moment of peak stress when diagnostic capability is greatest. Generally, the physical motion of the body caused by exercise generated stress diminishes the image quality or requires a time lapse resulting in suboptimal diagnosis.

Fourthly, exercise stress testing by physical motion is generally inconvenient to both patient and doctor. For example, a maximal stress test exhausts most patients and involves a significant recovery time. Additionally, maximal stress tests involve a degree of risks for the patient of falling which is directly related to the use of a tread mill. Because of the physical movement associated with the exercise, placement of the electrodes is also a problem. Specially designed electrodes which minimize motion artifacts must be securely attached. Finally, placing the electrodes can involve shaving the chest for a man, and sometimes burnishing the skin to achieve appropriate electrode contact.

Taken as a whole, these drawbacks make exercise stress testing an inconvenient test for both patient and physician. Because of its inherent difficulty, lack of sensitivity, lack of specificity, and cost, exercise stress testing is not generally recommended for asymptomatic individuals.

It is desirable to perform diagnosis for coronary artery disease by methods which can stress the heart in a manner which mimics aerobic activity while not forcing the patient to actually engage in strenuous physical activities. A test wherein the heart is stressed without the need for physical exercise would be not only of great practicality, but would also allow for the testing of individuals who heretofore have been unable to engage in exercise stress testing.

Various drugs exist which elicit acute and adaptive cardiovascular responses similar to the types of responses elicited by aerobic activity. They will be referred to as Exercise Simulating Agent beta agonists or "ESA™ Beta Agonists" for purposes of this invention. Generally, these drugs are catecholamines. Catecholamines are essential compounds in the body and play many important roles. For example, adrenaline and noradrenaline are natural catecholamines which act as neurotransmitters and hormones, controlling among other things, the function of the heart muscle. During physical exercise for an exercise stress test, adrenaline and noradrenaline are released, increasing the rate and force of contraction of the heart and blood pressure. These natural catecholamines do not act selectively on the heart, however, and have side effects which make them unsuitable as agents to pharmacologically stress the heart.

Several groups have described the intravenous infusion of synthetic catecholamines. In one example, U.S. Pat. No. 3,987,200 entitled "Method for Increasing Cardiac Contractility" issued to Tuttle et al. on Oct. 19, 1976, discloses a synthetic catecholamine dobutamine. Dobutamine elicits certain specific cardiac responses without the adverse side effects that would accompany administration of a natural catecholamine. Dobutamine exerts a positive inotropic effect (increasing heart contractility) without inducing arrhythmia and with minimal heart rate and blood pressure effects. When infused intravenously at high doses, dobutamine elicits increases in heart rate, myocardial contractility, arterial blood pressure, and coronary and skeletal muscle blood flow. Such responses resemble the effects of physical exercise. Although the heart rate does increase with infusion of dobutamine, the drug was designed to specifically minimize this effect. Increasing heart rate is referred to as positive chronotropic effect.

More recently, the novel catecholamine analogue, arbutamine, has been developed. Arbutamine appears to act selectively on the heart and cause an increase in the rate and force of contraction of the heart and blood pressure. Arbutamine is described in detail in Tuttle et al. "Diagnosis, Evaluation and Treatment of Coronary Artery Disease by Exercise Simulation Using Closed Drug Delivery of an Exercise Simulating Agent Beta Agonist", Ser. No. 308,683, incorporated by reference, above. Arbutamine is a catecholamine analog designed to stress the heart pharmacologically. Arbutamine produces a dose-dependent cardiovascular response similar to that of physical exercise. Accordingly, the heart rate can be increased incrementally by gradually increasing the amount of drug administered. Generally, the duration of action of arbutamine is short, and when drug delivery is terminated, the heart returns to a normal range of activity within a period of time similar to that which occurs after physical exercise. Tuttle et al. contemplate a closed loop drug delivery system in which the response variable (e.g., heart rate) is monitored for effect caused by the input variable (e.g., drug infusion rate). Computer control of the closed loop drug delivery is contemplated. The drug delivery device administers arbutamine to the patient, monitors the patients heart rate and optionally blood pressure, and controls the rate of drug delivery to obtain the desired heart rate. This system is advantageously useful in connection with widely used cardiac testing procedures, such as ECG, echocardiography and radionuclide imaging.

Ordinarily, drug delivery systems are control systems having an input-response relationship. A drug input, such as an absolute amount or an infusion rate, produces a physiological response related to the input. Typically, the input (such as drug infusion rate) is used to control some parameter associated with the response variable, such as a desired rate (heart rate, blood pressure level, etc.).

Broadly speaking, drug delivery systems are either open loop delivery systems or closed loop delivery systems. An open loop drug delivery system is one in which the drug is delivered at a predetermined rate without any direct or automatic adjustment in response to physiological response variables. A closed loop drug delivery system is one in which a drug is delivered in automatic response to feedback of a physical signal or response, which could include responses such as heart rate, blood pressure, ECG parameters, heart output or other similar physical response.

While numerous types closed loop systems exist, representative categories of control schemes include: linear-nonlinear, deterministic-stochastic, and adaptive-nonadaptive. More particularly, closed loop delivery systems include predictive type and proportional-integral systems. In a predictive system, the input quantity is correlated to the difference between the current value of the response variable and the desired or target level (i.e., error term). The proportional-integral systems utilize a proportionality error term plus an integral error term, each having different contributions to the overall input amount.

Closed loop drug delivery systems have been used for therapeutic purposes to maintain a physiologic parameter. One specific example is the use of a closed loop drug delivery system to control infusion of Nipride to control a patient's blood pressure. Such a system is described in Petre et al., "Infusion Pump Control", U.S. Pat. No. 4,392,849. Such a system is designed to maintain stability of a physiological parameter, as opposed to variation of that parameter for diagnostic purposes. Yet further examples of closed-loop drug delivery systems for therapeutic purposes are disclosed in Newman, PCT Application WO 88/08729, entitled "Iontophoresis Drug Delivery System", published Nov. 17, 1988. Various therapeutic closed-loop drug delivery applications are mentioned, including for medication delivery, control of blood pressure, insulin delivery and administration of pain killing drugs.

There are many unique and important obstacles presented in effective diagnosis utilizing a closed loop drug delivery system, especially for diagnosis of the heart. For example, there is potentially a long time delay for arrival of the drug at the target organ, that being the time between the administration at an intravenous or transdermal location and arrival at the heart. Secondly, it is quite often the case that various patients respond differently to a given drug, making response predictability more difficult. Third, there is the possibility of excessive build up of a drug in a patient. Fourth, safety monitoring for a contra-response must be done, and drug delivery terminated. Finally, monitoring the heart rate is a difficult signal to track as the heart rate is a very noisy signal.

Despite the clear desirability of a system which is effective in the diagnosis and management of CAD, no effective system has been known heretofore.

SUMMARY OF THE INVENTION

A closed loop drug delivery system uses patient response and rule based decision making methods to achieve operator specified responses for diagnostic purposes. In the preferred embodiment, the system causes stress thus allowing cardiac diagnosis by administration of an exercise simulating agent drug to pharmacologically stress the heart. The physiological response may be monitored by any known method, including ECG, echocardiography and radionuclide imaging. An acute cardiovascular response is achieved like that induced by physical exercise. Specifically, the results include increased heart rate, increased cardiac contractility and increased systolic blood pressure levels. As a result, increasing the heart's demand for blood and oxygen helps reveal diseased arteries which cannot supply the blood to the heart.

The overall drug delivery device consists of a hardware system and an expert, rule based, control system.

The hardware system acquires various physiological parameters of the patient and further receives operator specified information and based upon the inputs, outputs the desired rate of ESA drug infusion. In the preferred embodiment the physiological parameters are the heart rate and blood pressure, and the operator specified information is a protocol. A microprocessor based hardware system is used. While one or more processors may be used, in the preferred embodiment a data acquisition processor functions principally to receive and distribute the patient's physiological response information, a display control processor functions principally to display information and to receive user specified information, and a drug delivery processor functions principally to determine the drug delivery rate. The drug delivery processor controls a drug delivery source, such as an intravenous infusion pump or transdermal iontophoretic delivery system. Optionally, various displays may provide information to the operator, with both hard key and soft key inputs available.

The method generally consists of determining the ESA drug infusion rate by reference to various rules for various modes, such as RAMP, HOLD, TARGET, and LEVEL, and transitions between modes, such as transitioning from RAMP to HOLD, based on measured physiologic values, such as heart rate.

More particularly, the method generally comprises the following steps:

Determining the individual patient response to the drug, such as onset delay for a particular patient. Patient specific information is used in conjunction with the rule based decision making. In the preferred embodiment, an initial open loop administration of a bolus of drug based on the patient's weight generates physiologic response data from which patient dose response parameters are determined.

The user specifies the particular heart rate protocol desired. A simple protocol would consist of setting a desired maximum heart rate and the desired rate of increase in heart rate. The user may specify any desired order or combination of heart rate targets. The user additionally specifies patient specific information, such as a patient's age and weight.

During the drug delivery phase, the ESA drug is administered to cause a physiologic response. When in the RAMP mode, the rate of increase in heart rate is more important than the actual difference between the target heart rate and the present heart rate. When the heart rate is approaching the target heart rate maximum, the drug delivery is modified to achieve the heart rate target with a minimum of overshoot. In the preferred embodiment, the amount of ESA drug is reduced or eliminated prior to reaching the target heart rate maximum.

Optionally, the user may enter the HOLD mode at any time. The HOLD mode seeks to maintain the heart rate at the level existing at the time the HOLD was initiated. Preferably, the HOLD heart rate is achieved with minimum overshoot. In the preferred embodiment, when a HOLD is called, the infusion rate is dropped, followed by resumption of infusion to a rate necessary to sustain the desired heart rate.

In one aspect of this invention, a protocol comprising at least a target heart rate and a plan to achieve the heart rate are defined prior to the drug phase, and the protocol may be modified after the drug phase has begun. In this way the operator may vary the protocol during the test so as to maximize the diagnostic results.

In another important aspect of this invention, a protocol is defined which includes a target value, a plan to achieve the target value and an acceptable zone of deviation from the plan. During the drug phase, should the patient physiological variable, such as heart rate, fall outside the acceptable zone of deviation from the plan, alternate rules are followed.

In another aspect of this invention, the measured physiologic parameter is filtered prior to use in the control method. In the preferred embodiment, the heart rate measured, such as by an ECG, is sent through a low pass filter to enhance performance of the control system. More particularly, a filter with an exponential forgetting factor is used along with clipping of outliers, which enhances the signal and reduces the response of the drug administration method to noise.

In yet another aspect of this invention, various alerts and alarms are used to warn of potential hazardous conditions, or to terminate drug administration in the event of a hazard. Advantageously, the alerts and alarms include such conditions as: a sudden change in a physiologic variable, such as blood pressure or heart rate, the condition where each or a combination of the heart rate and blood pressure are in a marginal condition or excessive heart rate.

Optionally, user oriented interfaces are provided for ease of operation. In the preferred embodiment, a display system provides data on patient condition and response, as well as an indication of the user specified protocol information. A soft key system is useable with the display to provide for flexible user input.

In summary, the various modes of RAMP, LEVEL, TARGET, and HOLD, and the transitions between any of them, such as RAMP to HOLD, are controlled by a rule based, expert system based upon action of the hardware to achieve the desired physiological response. A protocol may be changed by the operator even after drug delivery has begun. Further, the control system itself will change administration rules if a patient response deviates from an acceptable zone.

Accordingly, it is a principal object of this invention to provide for improved diagnosis, prognosis and management of coronary artery disease.

It is yet a further object of this invention to provide for effective physiological stress of a patient without physical exertion of a patient.

It is an object of this invention to permit stress testing of patients who could not otherwise be tested due to an inability to exercise.

It is yet a further object of this invention to permit enhanced echocardiography and radionuclide imaging of patients under stress condition.

It is yet a further object of this invention to enhance patient safety, such as by reducing overall drug dosage.

It is yet a further object of this invention to provide a HOLD mode which achieves the desired heart rate with a minimum of overshoot, which enhances safety by not requiring a restart, thereby reducing total drug dosage, and which reduces the total testing time.

It is yet a further object of this invention to provide various alerts and alarms to enhance patient safety.

DETAILED DESCRIPTION OF THE INVENTION

Overview of the System and Method

Figure 1:
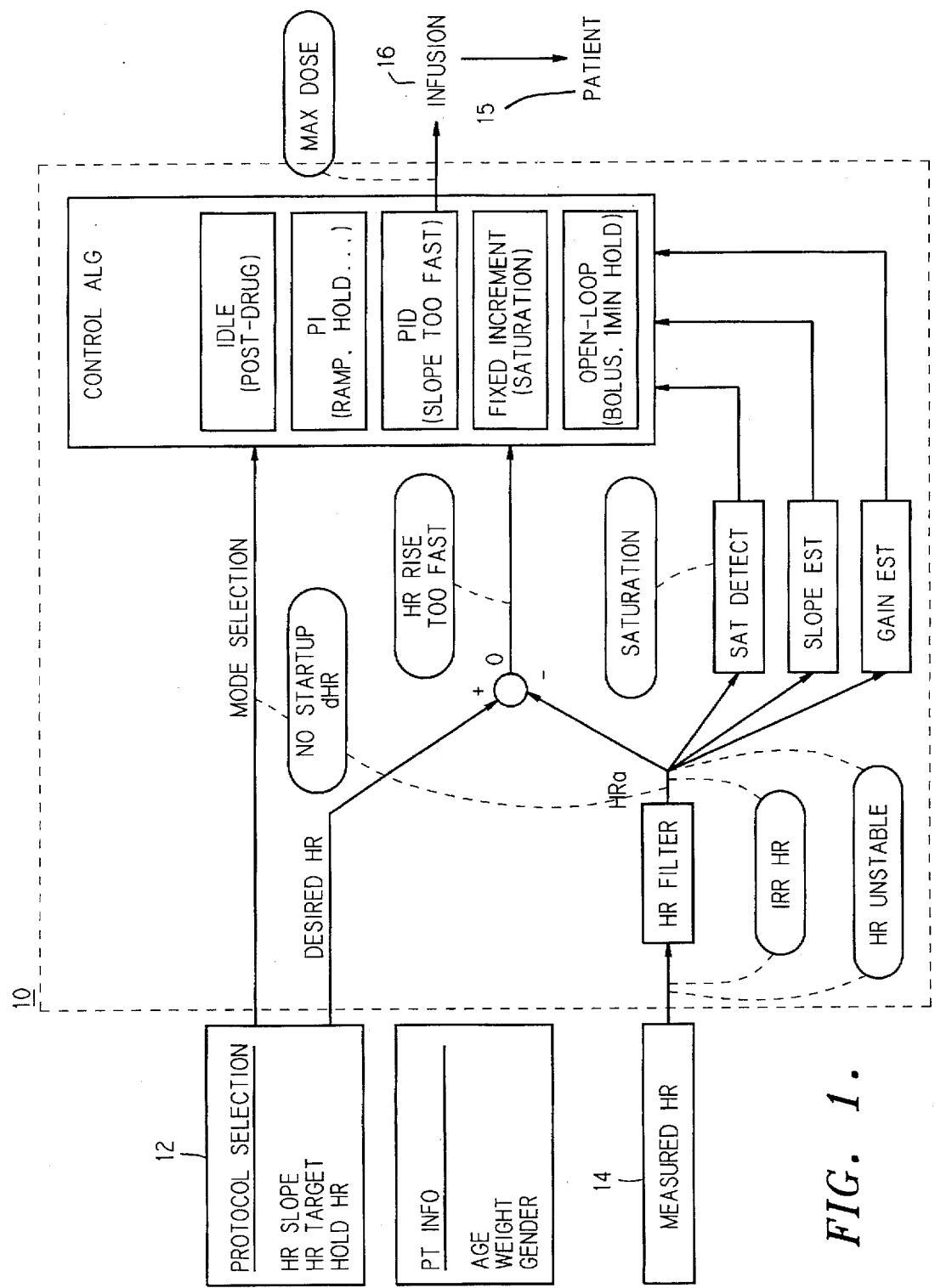
FIG. 1 is a block diagram of the overall control system.

FIG. 1 shows a block diagram of the ESA system 10. The ESA device 10 receives operator inputs 12, including the operator specified protocol (such as heart rate slope, heart rate hold and target heart rate) and patient information such as weight, age and gender. The ESA device 10 additionally receives physiological parameter inputs 14, such as heart rate and optionally blood pressure of the patient 15. The ESA device 10 provides various forms of outputs, including display outputs which provide information to the operator. The ESA device 10 outputs the drug 16 infusion rate or the drug itself if the drug delivery mechanism is included within the ESA device 10. Finally, the ESA device 10 outputs various alerts and alarms to warn the user of specified conditions or to terminate drug administration.

The physiological input of measured heart rate 14 when input to the ESA device 10 goes through a heart rate filter to produce an average heart rate (HRa). At this time the alerts and alarms for irregular heart rate and unstable heart rate may be activated if appropriate. The operator inputs 12 are provided to the control system, and include the input of MODE selection. The operator input 12 also includes the desired heart rate target which, during operation, is utilized in conjunction with the computed average heart rate to generate an input to the control system. The alert for no start up differential heart rate is derived from the heart rate average and MODE selection. Additionally, the average heart rate is used for saturation detection, and the associated alert or alarm for saturation, slope estimation and patient gain estimation. These in turn are provided to the control system as inputs. Based upon these inputs to the control system, the output of the control system is used to control the infusion 16. An alert or alarm for maximum dose utilizes the output from the control system. The maximum dose rate and the maximum total dose may be monitored as desired.

Figure 2:
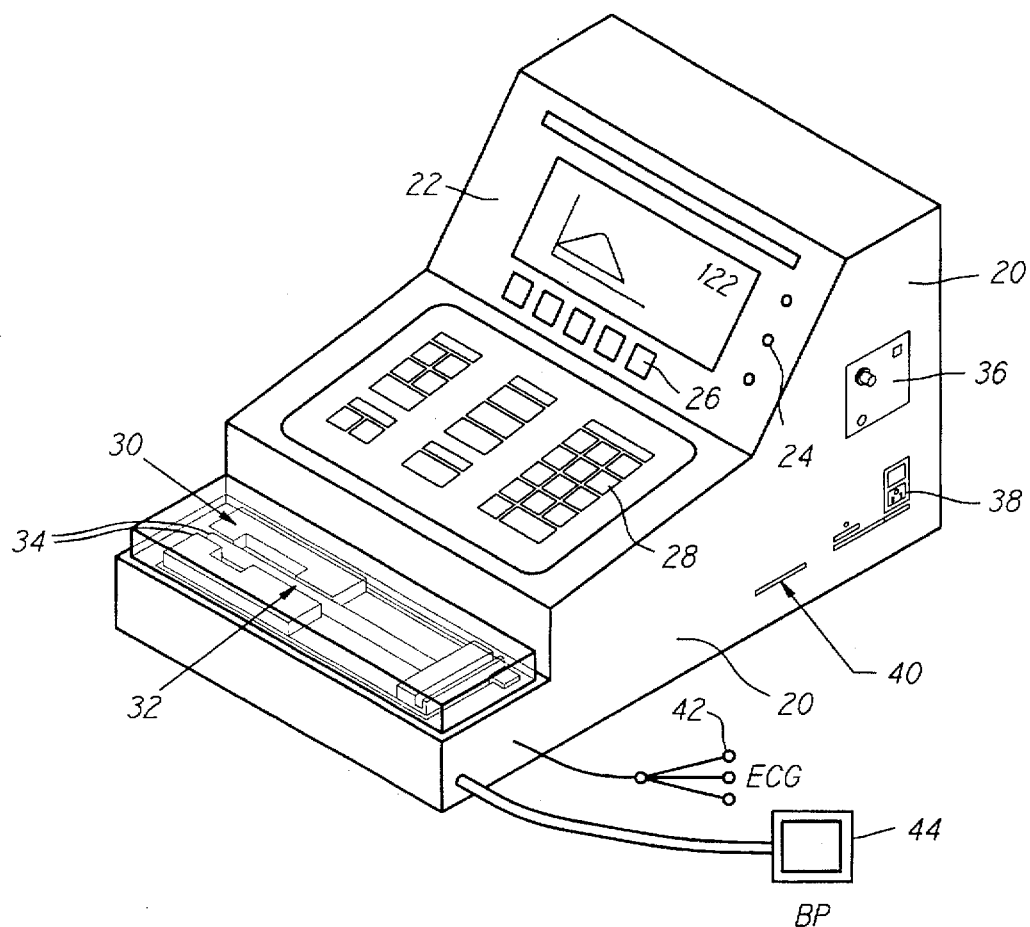
FIG. 2 is a perspective view of the ESA device.

FIG. 2 shows a perspective view of one design for the ESA device. A housing 20 generally includes a monitoring system, drug delivery controls and a drug delivery mechanism. In the preferred embodiment the monitoring system includes a screen 22 for display of information for the operator, system status lights 24 and soft keys 26. The display 22 is conventionally used to display an indication of the function of the soft keys 26. The drug delivery controls include various hard keys 28, which optionally include LEDs within them. The hard keys 28 may be used to enter, by way of example, the heart rate protocol (such as heart rate target, heart rate slope, or HOLD heart rate), numerical data such as a patient's age, or may cause other actions such as alert and alarm silence. The drug delivery mechanism may consist of any known form, whether intravenous or transdermal drug delivery. In the preferred embodiment, an IV pump 30 drives a syringe 32 to deliver the ESA drug via an intravenous (IV) administration set and catheter 34. The housing contains various functional elements such as an on/off switch 36 and an AC power receptacle 38. Optionally, a data transfer port, such as an RS-232 connector 40, is included. ECG leads and non-invasive blood pressure cuff 44 are attached through the housing 20.

Figure 3:
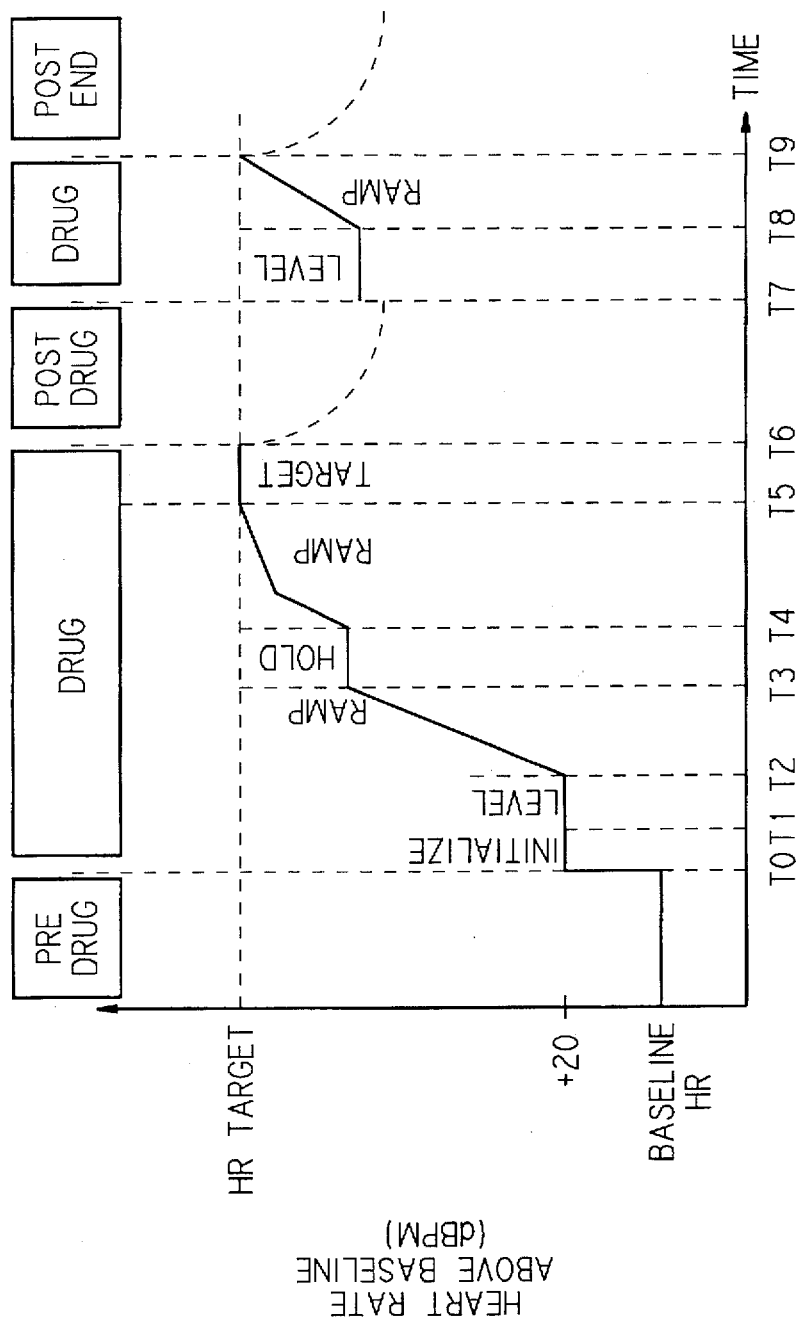
FIG. 3 is a graph of heart rate versus time showing various control modes.

The drug administration method may be broadly classified into three time periods—predrug, drug and postdrug. FIG. 3 shows a plot of heart rate versus time. The predrug, drug and postdrug periods are labelled above the graph.

The predrug time period is considered to be from when the monitoring leads 42 are attached (in the case of ECG monitoring) to start of drug administration. During this time a patient's baseline is established, principally for resting heart rate and blood pressure. During this period, the operator may enter patient related information such as age, weight and gender on the hard key pad 28. Further, the operator would specify the protocol, typically consisting of at least a heart rate target (e.g., 60 beats per minute over baseline) and the desired heart rate slope (e.g., increase of 8 beats per minute per minute). Finally, during the predrug period the operator would typically prepare the drug syringe 32 and IV administration set and catheter 34, or if a transdermal delivery system is used, prepare the drug delivery electrodes.

In FIG. 3, the baseline heart rate is shown prior to the time T0 and the heart rate target is labelled on the y-axis and marked with a horizontal dotted line.

The drug phase begins with the initial administration of drug and ends when drug administration is stopped. An initial bolus of drug is provided to the patient, and the patient response in heart rate monitored. During the drug phase, various operational modes exist. Among these modes are the LEVEL mode, the RAMP mode, the TARGET mode and the HOLD mode. FIG. 3 shows the LEVEL mode from time T1 to T2 and from T7 to T8, the RAMP mode from times T2 to T3, T4 to T5 and T8 to T9, the TARGET mode from T5 to T6, and the HOLD mode from time T3 to T4. The LEVEL mode occurs early in the drug cycle and is characterized by a generally uniform heart rate. The RAMP mode occurs during the drug phase and is characterized by a rate of increase in heart rate. The TARGET mode occurs during the drug phase and is characterized by a decreasing rate of heart rate increase. The HOLD mode occurs during the drug phase and is characterized by a relatively uniform heart rate. In addition to the various operational modes themselves, there are transitions from mode to mode such as from RAMP to HOLD. The drug phase is exited when the operator issues a stop or interrupt, or an alarm is generated by the ESA device, or the heart rate target is achieved.

The postdrug phase begins when drug administration ends. During this period, the heart rate and blood pressure of the patient are monitored. As shown in FIG. 3, the heart rate in the postdrug phase, T6 to T7 and after T9, decreases after drug administration ceases, in a manner not unlike heart rate response following termination of exercise.

As shown in FIG. 3, protocols may go from a postdrug phase to a further drug phase, shown at the transition time T7.

Filtering of the Measured Physiologic Parameter

The ESA device 10 receives the heart rate signal from a source, such as an ECG monitor. The measured heart rate can be a very erratic signal. Because of the large variability in the heart rate signal, a low pass filter is preferably used to extract the slower dynamics corresponding to the response of the heart rate to drug infusion. Additionally, since the heart rate serves as the feedback signal to the control system, large or frequent outliers, that is signals falling outside an expected window around the heart rate, would introduce undesired fluctuations in the infusion rate profile. On the otherhand, excessive averaging would distort the heart rate signal and present an incorrect patient profile to the control system.

Figure 4:
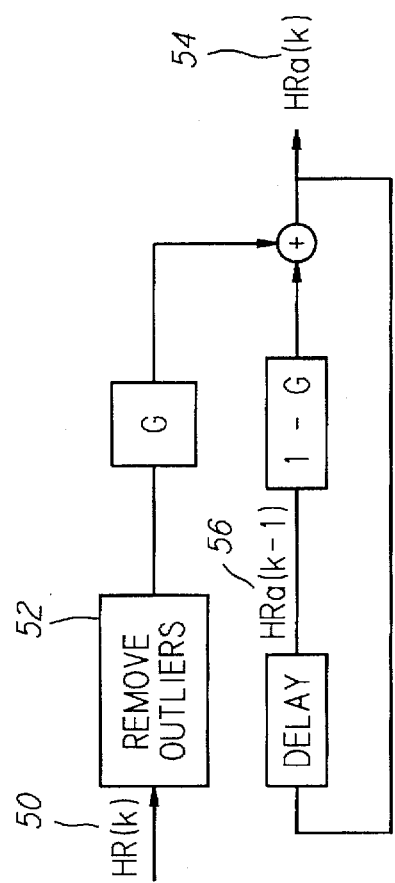
FIG. 4 is a block diagram of the HR input filter system.

FIG. 4 shows a block diagram of the basic filtering method of the preferred embodiment. The measured heart rate HR(k) 50 represents the unfiltered signal as supplied from the patient monitoring device. The unfiltered heart rate signal HR(k) has the outliers removed 52 prior to averaging. The output of the filter circuit is the filtered average heart rate HRa(k) 54. In the preferred embodiment, the average heart rate HRa(k) 54 is derived from an averaged signal having an exponential forgetting factor. A fraction G is summed with a fraction 1 minus G of the preceding averaged heart rate signal HRa(k−1) 56. Typically, sampling is done every 5 seconds.

In the preferred embodiment, the following method and parameters have proved useful for filtering the heart rate to enhance operation of the drug administration control. To obtain the heart rate from the peak to peak interval (called "rr") measurement from the ECG signal, the following calculation is performed:

$$\overline{rr}(t+1) = \frac{7}{8} * \overline{rr}(t) + \frac{1}{8} * rr(t+1). \quad (1)$$

The heart rate at time t is given by:

$$HR(t) = \frac{60}{\overline{rr}(t)}. \quad (2)$$

The heart rate value is updated every time a new R-wave is detected. The control system samples this HR signal every 5 seconds to acquire a new value for feedback control.

The following heart rate filtering rules were discovered based on actual test data, and generally provide for outlier clipping where a measured signal is either more than 6 beats per minute above or 8 beats per minute below the average heart rate. The following rules have proved effective in successfully filtering input heart rate.

$$HRdiff(t+1) = HR(t+1) - HRa(t)[-8 < HRdiff < 6] \quad (3)$$

$$G(t+1) = (G(t)/(1+G(t))) + 0.04;$$

$$G(0) = 1 \quad (4)$$

$$HRa(t+1) = HRa(t) + (G(t+1) * HRdiff(t+1));$$

$$HRa(0) = HR(0) \quad (5)$$

Establishing a Baseline Heart Rate

During the predrug phase, the baseline heart rate is established. The baseline heart rate is defined as the average heart rate at the initial start of drug delivery. FIG. 3 shows the baseline heart rate as the heart rate on the y-axis prior to the time T0. In the preferred embodiment, the control method determined heart rate changes relative to the baseline heart rate. Accordingly, it is important that an accurate baseline heart rate is established.

There are several conditions which indicate that a patient's heart rate has not reached a baseline or that the control system does not have sufficient data from which to calculate the baseline heart rate. In either of these cases, a nonacceptable condition or value (such as a heart rate of zero (0)) is returned as the baseline heart rate, indicating that drug initiation must be delayed until a valid baseline heart rate has been established. In the preferred embodiment, any of the following conditions will prevent the baseline heart rate from being established:

(1) Receiving less than two minutes (24 samples) of valid ECG measurements.

(2) Presence of an excessively low heart rate, e.g., heart rate less than 26 bpm, or excessively high heart rate, e.g., heart rate more than 120 bpm, while the baseline is being established.

(3) An ECG lead coming loose, the baseline heart rate being reset to a nonacceptable condition or value (e.g. zero heart rate) for half a minute.

(4) The existence of an "irregular heart rate" condition, which is defined to be an absolute (positive or negative) difference of more than 20 bpm between the measured heart rate and the averaged heart rate (HRa) for 2 consecutive samples.

(5) The presence of excessive noise in the measured heart rate signal, which in the preferred embodiment is measured as the variance (or sum of the square of the error between the measured heart rate around the current running average HRa). The variance is estimated using the following formula:

$$smsq(t+1) = smsq(t) + (c * ((HR(t) - HRa(t))^2 - smsq(t)))$$

where $$smsq(0) = 20; \text{ and } c = 0.1 \quad (6)$$

Excessive noise may indicate a problem with the ECG leads or the R-wave detection. The constant "c" determines the rate at which the estimated sum of the squares will be updated with information from newly acquired data. In the preferred embodiment, the estimate of the noise variance is not updated if any of the following conditions exists:

(1) an irregular heart rate condition is detected, (2) the ECG leads are off, or (3) an uninterpretable heart rate, that is, excessively low or high heart rate, is observed. If the estimate of the noise variance exceeds 100 bpm$^2$, the baseline heart rate is set to a nonacceptable condition or value (e.g. zero heart rate). Optionally, if the estimate of the noise variance exceeds 200 bpm$^2$, an alarm is sounded.

THE DRUG PHASE

Once a valid baseline heart rate is established and the other pre-drug phase requirements satisfied (such as setting of protocol and establishing the drug-delivery system), the drug phase may be entered.

Drug Response

Figure 5:
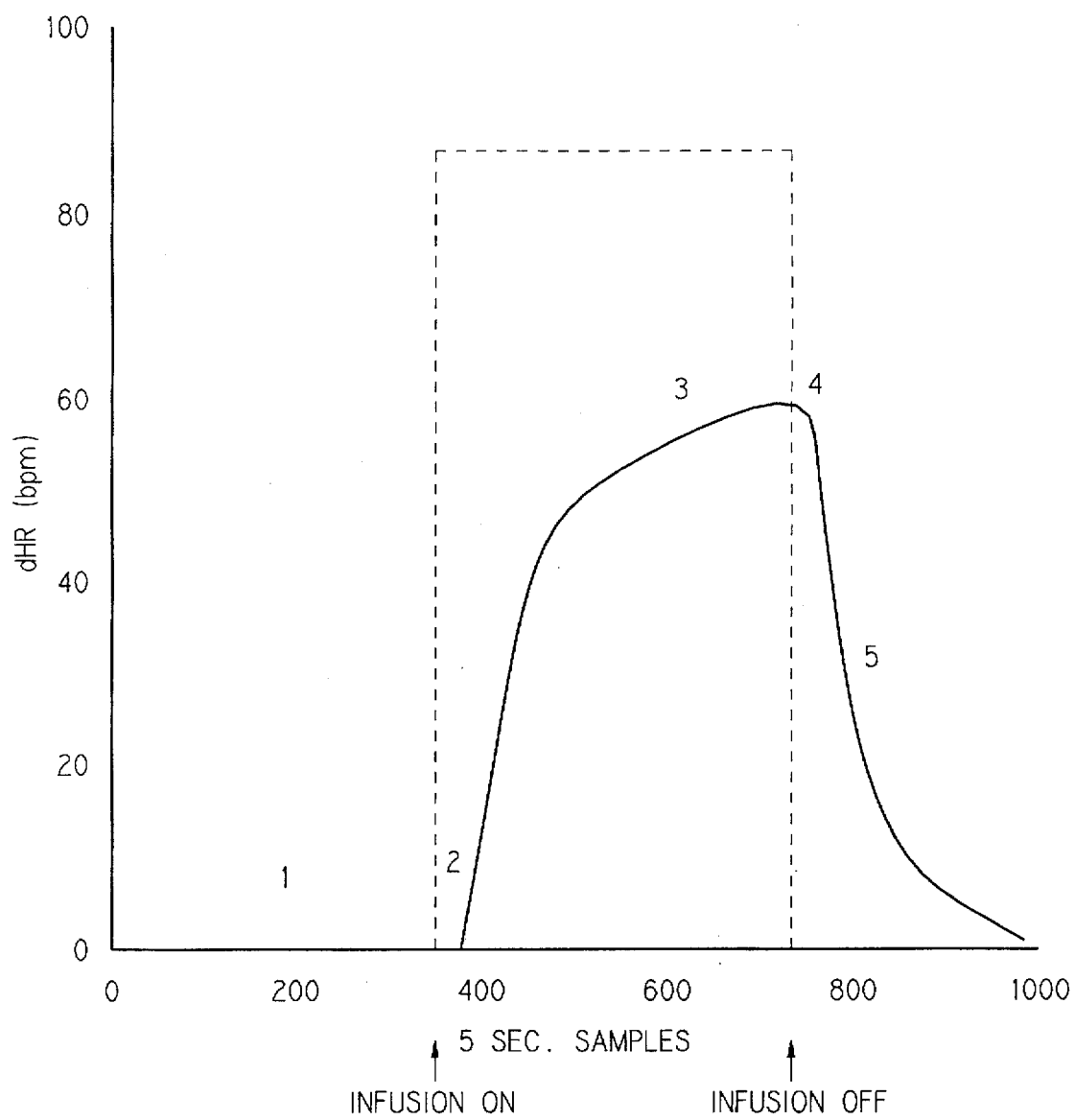
FIG. 5 shows heart rate response and infusion rate for a constant infusion of drug as a function of time.

FIG. 5 shows a typical response curve of the heart rate to constant infusion of arbutamine, the ESA drug. The change in heart rate from the baseline value is shown on the y-axis on the left, and the drug infusion rate (μg/kg/min) is shown on the right hand y-axis. Drug infusion incurred at approximately time 350 and ends at approximately time 715, with a constant infusion rate of 0.25 μg/kg/min. There is an onset delay between the time drug infusion begins and a perceptible increase in heart rate is measured. The onset delay is labelled 2 in FIG. 5. Typically, the onset delay is approximately 1 minute for arbutamine. The onset time or time needed to achieve steady state heart rate corresponding to a constant infusion rate, is labelled by 3 on FIG. 5. The offset delay, the time during which heart rate continues at preexisting levels after the infusion is stopped is labelled 4 on FIG. 5. The offset delay is approximately the same as the onset delay for arbutamine. The offset region is that after the offset delay, labelled 5 in FIG. 5.

Pharmacodynamic analysis of arbutamine establishes that there is a threshold level of action to achieve heart rate response. Typically, minimum infusion rate of 0.05 μg/kg/min. is necessary to observe a change in heart rate sufficient to distinguish it from the noise level.

The Initialization Mode

The initialization mode is shown at time T0 in FIG. 3, and represents the first stage in the drug phase. At the beginning of the ESA test, an effective threshold level of drug must be established, and the onset delay overcome. In the preferred embodiment, an open loop 1 minute bolus of arbutamine is delivered at a constant infusion rate of 0.1 μg/kg/min. Based upon pharmacodynamic analysis, the onset delay averaged 80 seconds, with the range being from 25 seconds minimum to 125 seconds maximum. Generally, the onset and offset delay is caused by the transport time from the point of drug administration to the heart and activation of the receptors. The pharmacodynamic studies further show that the time constant for onset to reach half maximum response value is approximately 5 minutes, whereas the offset time to decrease to half maximum is 7.5 minutes. The difference between onset and offset half maximum times is believed to be caused by a difference in association and disassociation of the drug with the beta agonist receptors of the heart.

Control in LEVEL Mode (T1)

FIG. 3 shows the LEVEL mode at time T1. After the initial bolus is delivered in the initialization mode (T0), the control method closes the feedback loop on the heart rate signal HRa and begins titrating the drug infusion. Titration begins at the 0.1 μg/kg/min. delivery rate established during the bolus administration. Initially, the control method target is set to plus 20 bpm above baseline during LEVEL control. While this start-up period is not essential, the following reasons weigh in favor of the LEVEL mode prior to beginning higher rates of drug infusion:

(1) Because of patient-to-patient variability in the onset delay, some patients may not have responded to the drug during the bolus period. If the control method target were to continually increase before a corresponding increase in heart rate occurred, an overly aggressive infusion profile could result.

(2) Because of variations in patient-to-patient gain (differential heart rate gain per unit drug infusion) the response in heart rate to the initial bolus may vary significantly. Providing a constant heart rate target during the LEVEL mode permits preliminary estimate of the patient profile to be established. The gain is preferably used in the control method for later modes.

(3) The start-up period is selected to allow the system sufficient time to show a response to drug infusion. Because of the fixed target and the conservative control during this period, the amount of drug infused will be limited.

The Proportional-Integral Control Method

In the preferred embodiment, a proportional-integral control method is used. The simple representation of the proportional-integral formula to calculate the control U(t) in discrete form is:

$$u(t) = kp * e(t) + ki * \sum_{l=0}^{Q=t} e(l) \quad (7)$$

where the tracking error is:

$$e(t) = trgt(t) - HRa(t) \quad (8)$$

with trgt being the value of the desired trajectory and ki and kp being the controller gains. The values for ki and kp for various modes is listed in Table 1.

TABLE 1

| | Level Mode | Ramp Mode | Hold Mode | Target Mode |
|---|---|---|---|---|
| kp | 4.0 | 4.0 | 2.0 | 2.0 |
| ki | 0.4 | 0.4 | 1.0 | 1.0 |

Equations 7 and 8 may be combined and written recursively as:

$$u(t)=u(t-1)+ki*e(t)+kp*(e(t)) \quad (9)$$

or:

$$u(t)=u(t-1)+k2*e(t)-kp*e(t-1);$$

$$k2=kp+ki \quad (10)$$

Because of the input-output delay in the system, the correction terms with e(t) are added to an average of the infusion rates over the last minute (12 samples), giving the following formula for the average value of u:

$$\bar{u}(t-1:t-12) = \sum_{i=t-1}^{t-12} \alpha(i) * u(i) \quad (11)$$

The complete proportional-integral formula for the control method is given by:

$$u(t)=\bar{u}(t-1:t-12)-k2*(HRa(t)-trgt(t))+kp*(HRa(t-1)-trgt(t-1)) \quad (12)$$

In the preferred embodiment, the weighing coefficient α (i) are selected as follows, to provide a stable but responsive infusion rate:

$$\alpha=\{0.1, 0.1, 0.1, 0.1, 0.1, 0.1, 0.2/3, 0.2/3, 0.2/3, 0.2/3, 0.2/3, 0.2/3, \} \quad (13)$$

When in a mode in which the target is constant, such as in the LEVEL or HOLD mode, the proportional-integral rule may be written more simply as:

$$u(t)=\bar{u}(t-1:t-12)+kp*(HRa(t-1)-HRa(t))+ki*(trgt(t)-HRa(t)) \quad (14)$$

Transition from LEVEL to RAMP Mode (T2).

The transition from LEVEL to RAMP mode is shown at time T2 in FIG. 3. At this time, patients are preliminarily classified into one of three response categories. An "average" response is one in which the heart rate at the end of the start-up period (bolus plus LEVEL time, typically 4 minutes) has reached a value between 10 and 20 bpm above baseline heart rate. This "average" response is associated with an onset delay of 75 seconds or 15 time periods. A response is classified as "fast" if the patient reaches a 20 bpm increase over baseline during the start-up period. This is associated with an onset delay of 60 seconds or 12 time periods. Once a plus 20 bpm increase in average heart rate is achieved, LEVEL mode (T1) is exited and RAMP mode (T2) is entered, even if this is before completion of the start-up period. A response is classified as "slow" if there is less than a +10 bpm heart rate response at the end of the start-up period. A "slow" response is associated with an onset delay of 90 seconds or 18 time periods. Because the heart rate response is close to the noise LEVEL in a "slow" response, optionally an alert is initiated. The onset delay estimated in this mode is used for the remainder of the ESA test, except in the case where a restart occurs at which time the test for onset delay estimation is preferably repeated.

At the time of transition from LEVEL mode to RAMP mode, the control method heart rate trajectory (desired heart rate) is initialized at the then current average heart rate HRa. This prevents a build-up of large differences between the control method trajectory and measured response. Further, the controller gains ki and kp are selected for RAMP mode control from Table 1.

RAMP Mode Control

In the preferred embodiment, the control method attempts to match the rate of increase of heart rate to the operator specified rate of increase. While a control method based upon the absolute difference between the target heart rate and the current heart rate could be used, the possibility of excessive drug infusion rates is less when the rate of increase in heart rate is the control parameter. The proportional-integral formula given above is utilized to calculate the infusion rate to elicit a physiologic response to match the desired rate of increase in heart rate. In the preferred embodiment, the infusion rate calculations are performed every 15 seconds, and the infusion rate adjusted accordingly.

There are two primary conditions which take the control method out of the proportional-integral control mode, those being the condition of saturation where the heart rate response is not increasing sufficiently, and over response where the heart rate is increasing too rapidly.

Saturation

In the case of saturation, it is has been observed that the increase in heart rate no longer increases or drops at higher infusion rates of arbutamine, typically around 0.3 μg/kg/min. An increased desired heart rate trajectory, combined with a saturation condition, could result in a steep increase in infusion rates if the proportional-integral control formula were to be strictly followed. A saturation detection mechanism in the control method detects saturation and alters the infusion rate, and optionally triggers an alert or alarm condition.

In the preferred embodiment, a peak detector tracks the last maximum average heart rate and the current sample index. If more than 30 seconds passes since the average heart rate exceeded the last maximum heart rate, the control method bypasses the proportional-integral formula. In such a case, the infusion rate is incremented every 30 seconds by a small amount. The control method switches back to the proportional-integral formula when the heart rate peak detector finds a new average heart rate maximum. In this way, rapid and unwanted increases in infusion rates are avoided during periods of saturation. Optionally, an alarm is sounded if an extended period of saturation persists or a decrease of 10 BPM of average heart rate occurs.

Excessive Rate of Increase

To determine if an excessive rate of increase in heart rate is present, the control method periodically calculates a value roughly equal to the rate of increase of heart rate. In the preferred embodiment, an estimate of the heart rate slope is calculated every 30 seconds. At 30 second intervals, the trailing average of the average heart rate over the last minute is calculated. The rate of increase is taken to be twice the difference between the new and old averages. If the slope exceeds the limit value for the specified rate of increase, the average infusion rate $\bar{u}(t-1:t-12)$ is scaled down according to the following formula:

$$scale=MAX(scalelimit, 1-(slope-limit)/(2* Desslope))$$

$$scale=MIN(10.0, scale)$$

where scalelimit is 0.97 (except the second time the estimated slope exceeds the desired slope ("Desslope") when scalelimit is 0.93), and "slope" is the actual rate of increase. Limit is set with the following table:

| | | |
|---|---|---|
| 4 ≤ Desslope ≤ 6 | (LOW) | limit = 6 |
| 7 ≤ Desslope ≤ 9 | (MED) | limit = 9 |
| 10 ≤ Desslope | (HIGH) | limit = 12 |

Transition Into HOLD Mode and Operation in HOLD Mode

The operator may demand a HOLD mode at any time. Because of the relatively substantial onset and offset delays for arbutamine, the drug already administered to the patient will cause an effect even after the HOLD mode command is received. In the preferred embodiment, it is desired to minimize the overshoot of the heart rate above the level for which a HOLD is desired. A smooth transition from RAMP to HOLD is desired.

Broadly, upon receipt of a HOLD, the control method decreases the drug infusion rate, often to a zero (0) infusion rate, and subsequently resumes infusion up to a rate necessary to sustain the desired heart rate level. Typically, the rate of drug infusion necessary during the RAMP mode will exceed the infusion rate necessary for a HOLD at a given heart rate, thus ordinarily, the final infusion rate is less than at the time HOLD was initiated. Preferably, the maximum duration of the HOLD mode is 5 minutes, and the minimum HOLD LEVEL is +20 bpm above baseline.

Somewhat conflicting requirements are presented between the RAMP mode and the HOLD mode. In the RAMP mode, it is desired to increase at the selected rate of increase, so as to most quickly achieve the desired heart rate maximum. However, when a HOLD mode is initiated, it is desired to minimize overshoot and to stabilize the desired heart rate with minimal transient response. The rule based system disclosed here provides for smooth response.

In the preferred embodiment, the steps for transition from the RAMP mode to the HOLD mode are as follows:

(1) The controller gains ki and kp are set for the HOLD mode as given in Table 1.

(2) The operator selected rate of increase and the infusion rate existing immediately prior to the HOLD mode request are saved for use in transition out of the HOLD mode.

(3) The control method targets are set as follows:
 If the HOLD mode is called during the RAMP mode, the control mode is set at +4 bpm above the average heart rate HRa at the time HOLD starts. Since the average heart rate HRa lags the measured heart rate during the RAMP mode, this addition adjusts the control method target to an operator perceived level.
 If the HOLD occurs during the start-up mode, the control mode target is set to the average heart rate HRa at the time the HOLD is called.

(4) The steady state infusion rate is initially calculated as follows:
 The estimated infusion rate ("E") is calculated based on estimated patient gain and HOLD target level according to the following formula:

$$E=(HOLD\ HR-baseline\ HR)/Pgain, \quad (15)$$

Where Pgain is a measure of the patient gain (see "Parameter Estimation", below).

If a RAMP mode was active for at least 2 minutes prior to the HOLD mode call, the pre-HOLD infusion rate (pHIR) is scaled relative to the estimated heart rate slope (described above) as set forth below:

| | | | |
|---|---|---|---|
| | (slopt + Desslope)/2 < 5 | scale = 0.9 | (16) |
| 5 ≤ | (slope + Desslope)/2 < 9 | scale = 0.8 | |
| 9 ≤ | (slope + Desslope)/2 | scale = 0.6 | |

The average of this value with the previously estimated infusion rate is used as the steady-state estimate of the infusion rate (R):

$$R=[E-(pHIR)*scale]/2 \quad (17)$$

This calculated infusion is bound by the maximum infusion rate then existing.

(5) If no saturation is detected and a RAMP mode precedes HOLD, a 1 minute open-loop control is used. In the preferred embodiment, the control method adjusts the infusion rate geometrically from 0 to the steady state level over a 1 minute interval according to the following rule:

infusion=steady-state infusion*(1.0−0.8$^i$);

$$i=1,\ldots,12 \quad (18)$$

Because transitioning is from the RAMP mode, the built up momentum in the system, coupled with the sudden switch to HOLD mode, can result in some overshoot due to the offset delay inherent in the system. However, by following the above rules, the overshoot is minimized and the HOLD value achieved.

Transition Out of HOLD Mode (T4)

The transition point from the HOLD mode to the RAMP mode is shown at T4 in FIG. 3. To improve the resumption of heart rate increase to the RAMP mode, the initial infusion rate is set to a different level. The following steps are used:

(1) The controller gains ki and kp are reset to the RAMP mode levels of Table 1.

(2) The control method target is reset to the present heart rate level HRa.

(3) The initial infusion rate is set according to the following rule:

Infusion Rate=0.6×(pre-HOLD infusion rate)+0.4×(end-HOLD infusion rate).

0.4×(end-HOLD infusion rate).

If the operator has decreased the desired heart rate slope by more than 3 beats per minute per minute during the HOLD, the prehold infusion factor is multiplied by 0.3 and the end HOLD factor is multiplied by 0.7.

Target Control (t5)

As the heart rate approaches the target heart rate, the control method acts to control drug administration in an attempt to avoid overshooting the heart rate target. This is typically effected by stopping infusion while the heart rate is still below the target heart rate. Because of the momentum in the system and the offset delay, the heart rate will still increase after infusion is stopped. This action may be taken according to the following rules:

(1) Once the average heart rate equals the heart rate target minus 2 times the selected slope, the control system slope is automatically set to 4 bpm per minute.

(2) The control system target is not permitted to exceed the operator selected target. If the control system target equals the operator selected target heart rate, the target mode is entered and the controller gains ki and kp are set as provided in Table 1.

Alternatively, overshoot may be reduced by imposing a rate of increase limit. For example, the maximum slope may be set to 8 BPM/min. when the average heart rate is within range such as 20 BPM) of the target heart rate.

Target Achieved (T6)

Two separate criteria are used to determine whether the operator selected heart rate target has been achieved. Satisfaction of either of these criteria will terminate drug infusion and initiate a transition to the post-drug phase. The criteria are:

(1) If a measured heart rate sample exceeds the target heart rate and the next two heart rate measurements remain above the value (heart rate target minus 5 bpm), then the selected target is deemed to be achieved. The control system stops drug delivery.

(2) During the RAMP mode, the heart rate slope is calculated (described above) and as a result of this estimate, a "threshold to target" value is calculated. The following define the threshold for ranges of the average of the computed slope and the desired slope ("AVERAGE"):

if AVERAGE<5, threshold=5;

if 5≦AVERAGE<9, threshold=8; and if 9≦AVERAGE, threshold=12.

When the average heart rate exceeds the value of heart rate target minus threshold target value, drug delivery is stopped and the heart rate target is deemed to have been achieved.

When in the HOLD mode, if either of these conditions exists, infusion continues but an alert is triggered if average heart rate is above the heart rate target. In this way, a HOLD mode may be entered despite its close proximity to the selected heart rate target.

Exit Drug Phase

In addition to achieving the heart rate target, a transition from drug phase to post drug phase happens upon any of the following events:

(1) activation of an alarm, (2) the operator issues an "interrupt" or "stop", (3) the HOLD mode exceeds 5 minutes, (4) the average heart rate is above the heart rate target during the HOLD mode for 2 minutes.

During the post-drug phase, the infusion rate is set to 0.

Restart to LEVEL Mode Control (T7)

It is possible to transition from the post-drug phase to a second drug phase. This may occur if the operator has designated such a protocol, or has made the requests after the first protocol of ramp to target heart rate or has remedied an alarm condition.

If the post-drug phase has been less than 30 seconds, the control system merely resumes in the RAMP mode. In the preferred embodiment, the control system is initialized at the previously saved infusion rate, and the control system heart rate target is set at the present heart rate level HRa. No LEVEL mode control is activated. However, if the post-drug phase lasts more than 30 seconds, a start-up period is inserted before the RAMP mode is resumed. The start-up period is set for 3 minutes. Typically, the heart rate will be declining during this post-drug phase. The restart period is used to stop the downward decline in heart rate and to reverse the decline toward an increasing rate. A constant target is set at 10 bpm above the present average heart rate HRa when restart was initiated. A "virtual baseline" is formed since the heart rate is typically declining and, owing to the onset delay, typically would decline a few beats per minute towards the virtual baseline prior to resuming an increase. The infusion rules for LEVEL mode after restart are as follows:

(1) If restart happens in the first 4 minutes of the test, infusion is initialized at 0.1 µg/kg/min.;

(2) Otherwise, the infusion rate is calculated from estimated patient gain and the control system target heart rate;

Infusion Rate=Target/Pgain.

(3) Calculated infusion rate is limited to the value of the previous highest infusion rate and by a rate depending on the desired heart rate slope as indicated in Table 2.

TABLE 2

| 4 ≦ Desslope ≦ 6 | limit = 0.15 µg/kg/min |
|---|---|
| 7 ≦ Desslope ≦ 9 | limit = 0.2 µg/kg/min |
| 10 ≦ Desslope | limit = 0.3 µg/kg/min. |

Finally, all registers which kept track of various variables, such as slope duration, slope estimation, target threshold and maximum heart rate, from the prior drug phase are reset.

RAMP Control After Restart (T8)

The RAMP mode after restart is shown after time T8 in FIG. 3. The transition to RAMP mode after the LEVEL mode at restart is analogous to that described earlier for the initial drug phase. The alert and alarm functions detecting a lack of start-up responses are also reactivated. The "virtual baseline" is taken to be the reference heart rate for restart.

Parameter Estimation

An estimate of patient gain is used to calculate infusion rates at the start of a HOLD mode and at the restart. The patient gain estimate is calculated on-line from a recursive least-squares parameter fit on the pharmacodynamic model given by the following equations:

$$HRa(t+1)+\alpha HRa(t)=\beta * u(t-n_k) \tag{17}$$

This patient gain can be related to the estimated coefficients $\alpha$ and $\beta$:

$$PGain = \frac{\beta}{1+\alpha} \tag{18}$$

EXEMPLARY RESULTS OF VARIOUS TEST PROTOCOLS

FIG. 6 through FIG. 9 show various possible test protocol sequences. All figures show the average heart rate and dosage rate as a function of time, with the average heart rate being shown as a solid line and the dose rate as the dotted line. The time is given in minutes, the heart rate in beats per minute and the infusion rate in micrograms per kilogram per minute.

Figure 6:
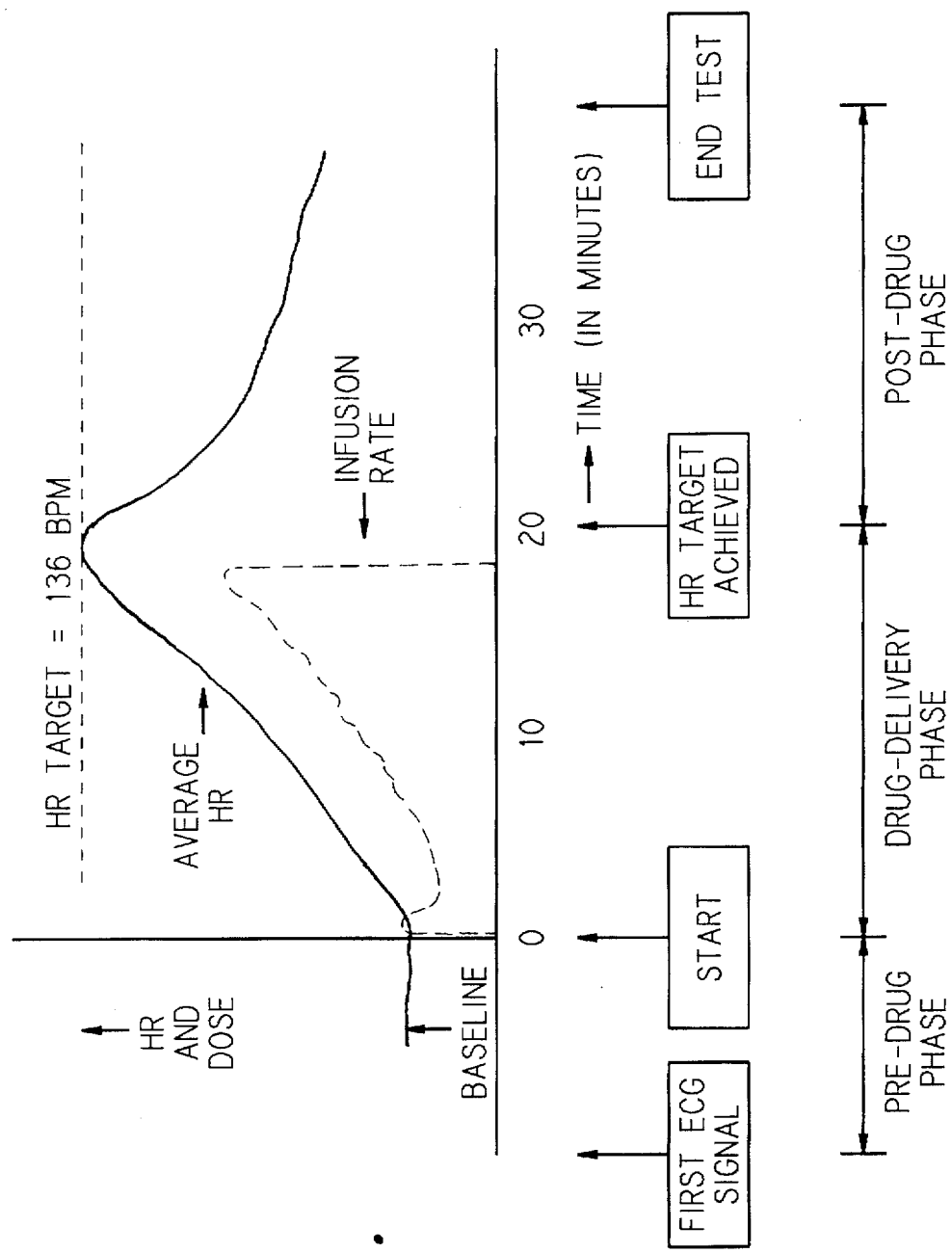
FIG. 6 shows the heart rate and drug delivery rate as a function of time for a protocol of a RAMP to a heart rate target.

FIG. 6 shows a programmed single rise to heart rate target. The assumed patient is a 60 year old male. In the preferred embodiment, the heart rate target is taken to the 136 beats per minute, calculated as 0.85×(220−60). The rate of increase of heart rate (slope) is set to a relatively low value of 4 bpm/min. The baseline heart rate value is established during the pre-drug phase (shown as the time before time 0). The drug delivery phase begins at time t0, with the open-loop bolus injection shown as the relatively higher injection rate. In the preferred embodiment, after one minute, the LEVEL mode is entered for which a heart rate target of +20 bpm is set. Around time t=4 minutes, the heart rate has begun to rise and the RAMP mode is entered. As the heart rate rises towards the heart rate target of 136 bpm, the infusion rate also rises. At time t=19 minutes, the system determines that the average heart rate will reach the heart rate target, and accordingly, terminates the drug infusion. After drug infusion stops, the heart rate reaches the target heart rate and begins its decline back towards the baseline heart rate.

Figure 7:
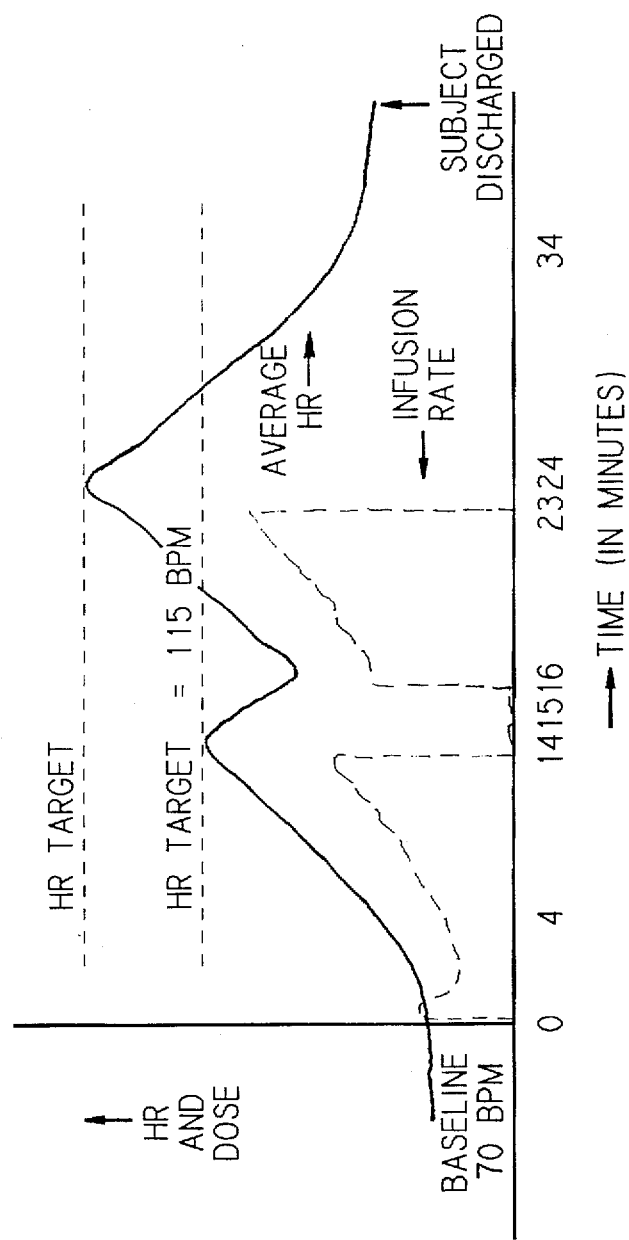
FIG. 7 shows the heart rate and drug delivery rate as a function of time for a protocol of a RAMP to a first heart rate target followed by a RAMP to a second heart rate target.

FIG. 7 shows a protocol having two heart rate rises to two different heart rate targets. Again, it is assumed that the patient is a 60 year old male and accordingly the heart rate target would be 136 bpm. Here, it is assumed that the user adjusts the heart rate target to 115 bpm, perhaps due to suspected coronary artery disease. As was the case with the single rise to heart rate target protocol described in connection with FIG. 6, the first rise to the heart rate target of 115 bpm follows a similar pattern to time of 14 minutes. The heart rate continues to rise briefly to reach the heart rate target and then begins to decline. The second target of 136 bpm is then set and drug delivery is restarted at t=16 minutes. The rate of drug infusion at t=16 minutes is computed based upon the rules described above. The heart rate decline stops and the heart rate resumes its upward climb in a RAMP mode. At time t=23 minutes, the method has determined that the infusion is sufficient that the heart rate will achieve the second heart rate target of 136 bpm, and accordingly is terminated. The heart rate reaches the second target and begins its downward decline to the baseline rate.

Figure 8:
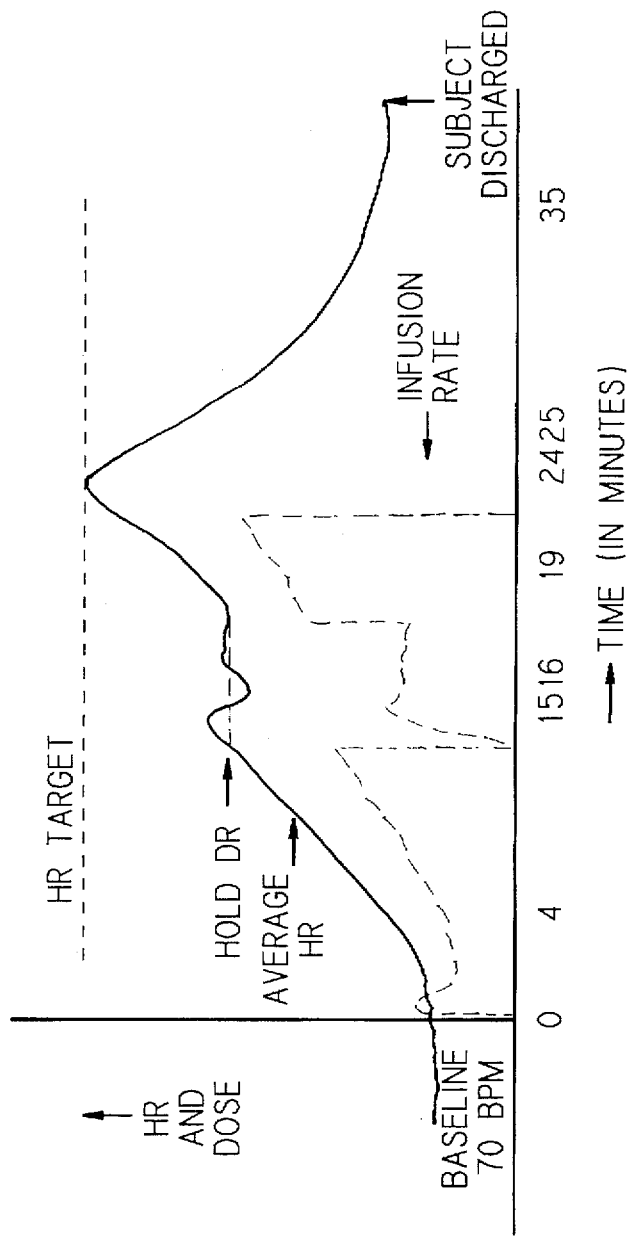
FIG. 8 shows the heart rate and drug delivery rate as a function of time for a protocol of a RAMP to a heart rate target, including a HOLD.

FIG. 8 shows a protocol of a single rise to a target heart rate, with the addition of a HOLD mode occurring at time t=15 minutes. The initial bolus, LEVEL mode and RAMP mode occur as described as above. When the HOLD is selected at t=15 minutes, perhaps due to the suspected indication of ischemia, the infusion rate immediately drops significantly and then increases infusion rate to a level estimated to provide maintenance of the heart rate at the desired level. Once the HOLD is finished and the RAMP restarted at t=19 minutes, the infusion rate is increased according to the selection procedures described previously. The RAMP mode and TARGET mode are then completed, with the heart rate reaching the target of 136 bpm followed by subsequent decrease to the baseline.

Figure 9:
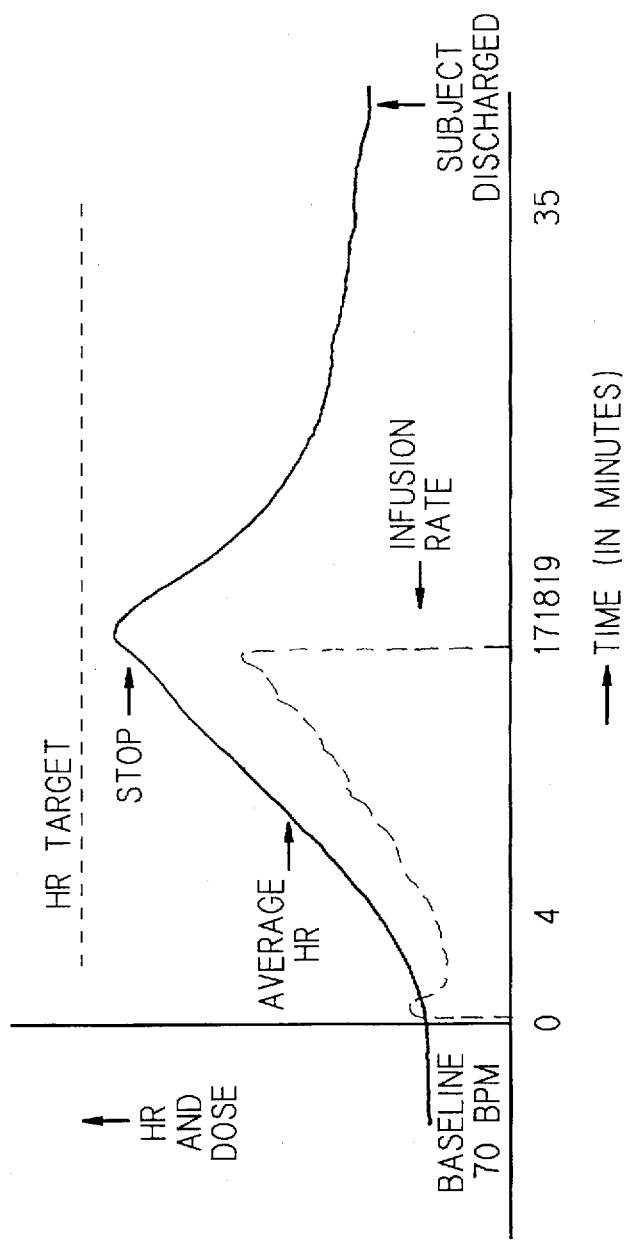
FIG. 9 shows the heart rate and drug delivery rate as a function of time for a protocol which revealed ischemia.

FIG. 9 shows protocol of a single rise, in which ischemia is revealed. Again, the same assumptions are made as in the case of FIG. 6, with the same infusion rates and responses up until time approximately t=15 minutes. At that point, if the user gets an indication of ischemia and desires to stop the test, pressing the STOP button immediately terminates this infusion (shown at t=17 minutes). While there is a slight continued rise in heart rate following termination of drug delivery, the heart rate soon begins its decrease. In the preferred embodiment, the patient is monitored for a relatively longer period following drug termination in a case revealing ischemia than in a case which does not indicate such a condition.

It will be appreciated that any useful diagnostic protocol may be used consistent with this invention. By combining RAMPs of various slope and duration, in combination with various lengths of HOLD, virtually any achievable desired heart rate may be specified as a function of time. A RAMP need not be linear, but may be any desired function of time.

ALERTS & ALARMS

Numerous alert and alarm criteria may be optionally implemented within the ESA device control program to detect hazardous conditions or unexpected patient responses to the drug. If an alarm is triggered during drug delivery, infusion is immediately terminated. The alarm condition remains in effect for a time period sufficient to permit the condition to dissipate, but not so long as to be annoying. In the preferred embodiment, this time is set for 30 seconds. By such a choice, should the operator elect to restart drug delivery, the 30 second time will require the restart to begin with LEVEL mode control. Alerts warn the operator of conditions that should be corrected within a short time, but do not stop drug delivery. The various alerts and alarms will be described below.

No Start-Up Increase in Heart Rate

It is necessary to verify that a patient is responding to a drug both at the beginning of the test and after a LEVEL mode restart. A "No Increase In Heart Rate" alert is activated if:

(1) At the beginning of a drug administration the average heart rate has not reached 10 bpm above baseline after 4 minutes (1 minute bolus plus 3 minute start-up).

(2) After a restart is initiated, if the heart rate average HRa is less than the heart rate average at the beginning of restart (after 3 minutes) the alert is activated.

The alert is cleared after 30 seconds. Three minutes later, the "No Start-Up Increase In Heart Rate" alarm is activated if the average heart rate maximum has not reached 10 beats per minute above baseline in the case of initial start-up or virtual baseline in the case of restart.

Increasing IV Dose, No Increase in Heart Rate

These alerts and alarms detect saturation condition. As previously described, the saturation condition occurs when the average heart rate does not exceed the last maximum average heart rate for a predetermined period of time. Table 3 indicates the time in 5 second samples between these two events which cause an alert or alarm.

TABLE 3

|  | HRmax <= 40 | | HRmax <= 55 | |
| --- | --- | --- | --- | --- |
|  | Slope <= 6 | Slope > 6 | HRmax > 40 | HRmax > 55 |
| Alert (T1) | 24 | 24 | 18 | 15 |
| Alarm (PT1/PT3) | 48 | 36 | 30 | 24 |

Preferably, the alert is not active during HOLD mode, start-up periods or prior to 1.5 minutes into the RAMP mode. The alarm is also triggered by either of the following conditions:

(1) A 10 bpm drop in the average heart rate HRa from the previous maximum, or (2) Heart rate average HRa is 15 bpm below the desired target during HOLD mode.

Optionally, an additional alarm condition may be set if the infusion rate is at maximum (typically 0.8 μg/kg/min.) and the IV dose is increasing but heart rate is not increasing. Another optional alarm condition may be set if the two alerts of 1) increasing IV dose, but no increase in heart rate and 2) falling systolic blood pressure occur at the same time. These alerts and alarms are preferably cleared 30 seconds after drug delivery is stopped.

Irregular Heart Rate

During the drug delivery and post-drug phases, the measured heart rate is compared to the averaged heart rate. If an absolute difference between the measured heart rate and the average heart rate exceeds 20 bpm, the average heart rate is stored. If the next measured heart rate again shows a difference of more than 20 bpm from the now stored averaged heart rate, the irregular heart rate alert is activated. If the alert persists for 30 seconds, the irregular heart rate alarm is activated. This advises the operator of short term irregularities in heart rate signal, such as excessive outlier values, and detects abnormal patient response to the drug. The alert is cleared whenever the difference between a new measured heart rate and the stored heart rate average is less than 20 bpm or 30 seconds has passed in the case of post-drug mode.

The Rapid Increase In Heart Rate Alert and Alarm

The rapid increase in heart rate alert is triggered if the average heart rate HRa exceeds the control system trajectory by 10 bpm. The alarm is activated if the alert condition persists for a period of time, such as 30 seconds or the average heart rate HRa exceeds the control system target by more than 20 bpm.

The Heart Rate Not Stable Alert and Alarm

The sum of the squares variance used in the pre-drug and drug phases, described above, is monitored to verify the quality of the feedback signal. An alert is triggered if the variance exceeds 100 bpm$^2$, corresponding to approximately to a "noise level" of 10 bpm. The heart rate not stable alarm is activated if the variance estimate exceeds 200 bpm$^2$, corresponding to a "noise level" of 14 bpm. The variance is not updated if (1) an irregular heart rate alert is active, (2) the ECG leads are removed or (3) an uninterpretable heart rate has been observed, such as heart rate below 26 bpm.

Maximum IV Dose Alarm

This alarm is activated if the total amount of drug delivered over the complete period of test meets a specified amount. For arbutamine, a clinical limit of 10 µg/kg is the upper limit. This alarm condition will not disappear until a new patient sequence is initiated. Optionally, the alarm flag may be cleared after 30 seconds to avoid undue operator irritation. However, further drug delivery is not permitted, and if attempted, a "maximum I.V. dose" alarm is reactivated.

The Heart Rate Over Target During HOLD Mode Alert

If the heart rate exceeds the operator selected maximum heart rate during a HOLD mode, drug infusion is not stopped, but the heart rate over target during HOLD alert is activated. This permits the operator to enter the HOLD mode at a level close to the maximum heart rate, but to avoid termination of drug delivery because of an erroneous heart rate target achieved due to overshoot when entering the HOLD mode. If the alert persists for 2 minutes, the target reached flag is set, which causes drug infusion to stop and the post-drug phase to be entered.

Alarm From Combination of Alerts

Even when a single alert condition may not justify terminating drug delivery, the existence of two or more alerts may justify an alarm condition. For example, alerts relating to heart rate and to blood pressure, each of which is merely on alert, may justify an alarm. A Falling Systolic Blood Pressure Alert plus a Heart Rate Saturation Alert existing together cause an Alarm.

USER INTERFACE

The user interface is preferably designed to permit ease of operation. Graphical representations of heart rate, blood pressure and average heart rate are provided to the user, as well as numeric indications of current actual and average heart rate and blood pressure. User operated keys, optionally soft keys, permit modification of heart rate trajectory during actual testing. Further, the interface permits rapid and easy initiation of a HOLD or STOP command.

DESCRIPTION OF THE PREFERRED HARDWARE EMBODIMENT

Hardware Specifics

The external aspects of the ESA device have been described in connection with FIG. 2. Internally, the main functional components may be grouped as follows: the data acquisition functions, the display control functions and the drug delivery control functions. The data acquisition functions serve to monitor the patient 15 (see FIG. 1) and to provide the physiological parameter information 14 to the ESA device 10. The display functional aspects provide the output display 18 plus various other formats of data output. The drug delivery control functional system controls the drug infusion rate based upon the drug administration method described herein.

These functional aspects may be performed by any form of hardware system which achieves the desired performance and functional characteristics of this invention. Either a single or multiple processor system may be used. The system may be analog or digital, or a combination of both.

Figure 10A:
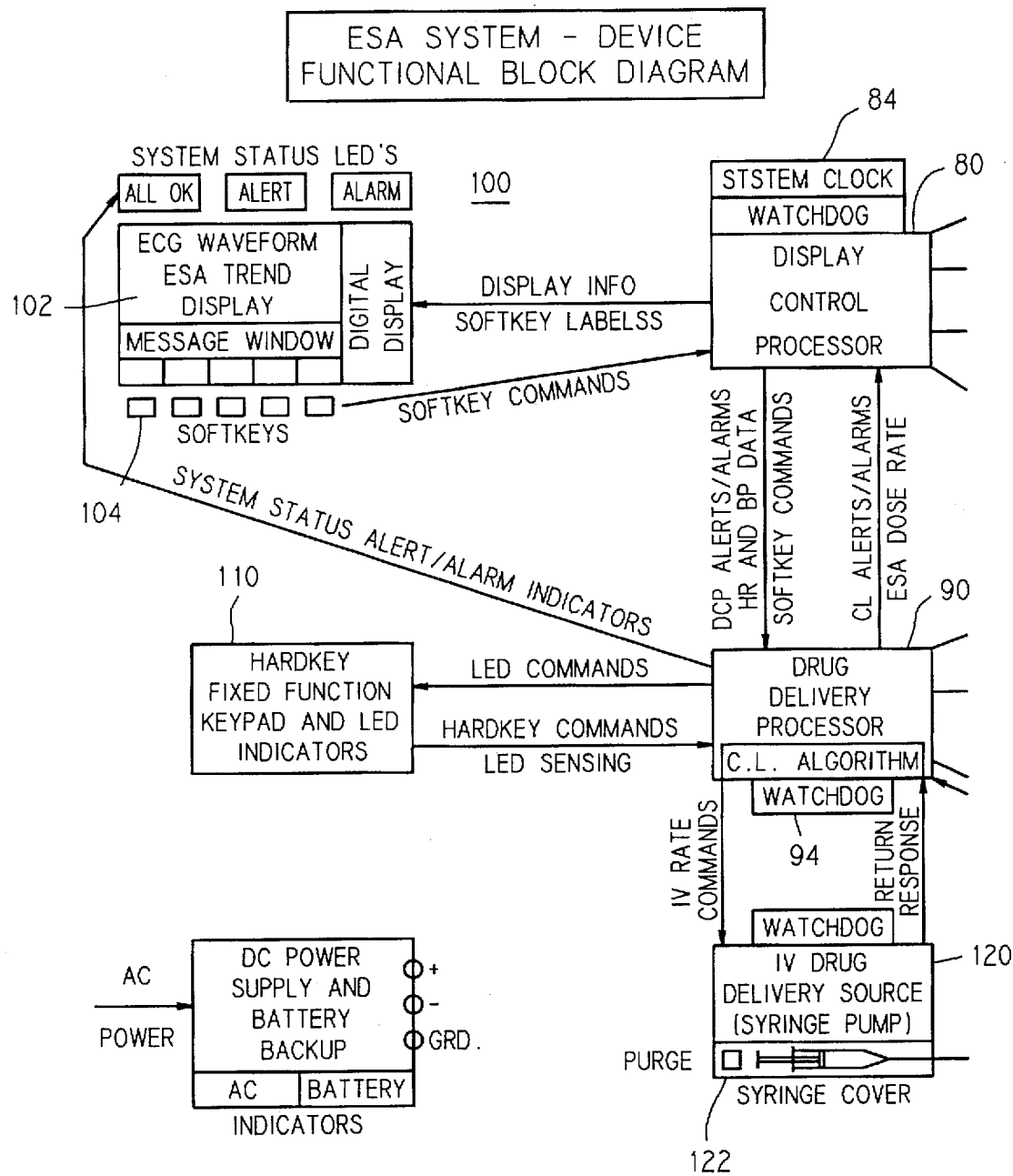
FIG. 10 is a block diagram of the hardware system.
Figures 10, 10B:
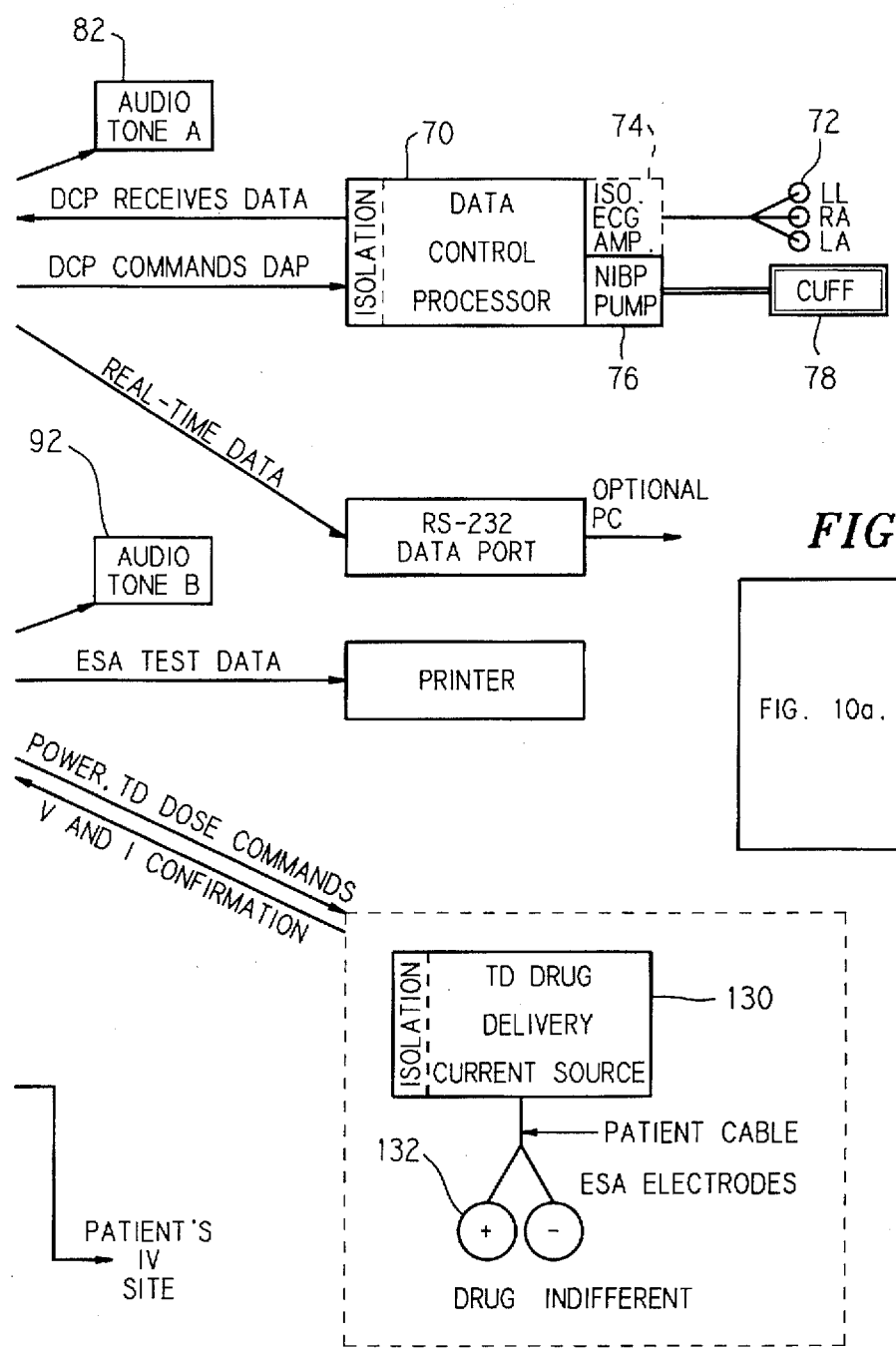

FIG. 10 shows a functional block diagram of the ESA device. In the preferred embodiment. Separate microprocessors are used for the various functional aspects of the system.

In the block diagram of FIG. 10, the data acquisition processor block 70 controls the data acquisition functions. The display control processor block 80 controls the display functions. The drug delivery processor block 90 determines the drug administration rate based upon the rules provided above.

The data acquisition processor 70 provides the interface between the patient and the overall ESA device. In the preferred embodiment, the patient is monitored for an ECG waveform through a 3 lead arrangement 72. An ECG amplifier 74 functions to drive the selected ECG lead 72, to electrically isolate the various ECG leads and to amplify the ECG signal prior to input to the data acquisition processor 70. Optionally, a non-invasive blood pressure measurement system is provided. A non-invasive blood pressure pump 76 inflates the cuff 78. Using any desired technique, the systolic and diastolic pressures are measured, and the pulse rate optionally determined. The data from the ECG amplifier 74 and non-invasive blood pressure cuff 78 are provided to the data acquisition processor 70. The data acquisition processor 70 filters the ECG signal, detects the QRS complex and calculates the heart rate. This information is then transferred to the display control processor 80. Optionally, electrical isolation of the patient monitoring connections is provided within the data acquisition processor 70.

The display control processor 80 serves the function of controlling the display and providing data transfer among the various processors. The display control processor 80 receives heart rate and blood pressure data from the data acquisition processor 70. This data is provided to the drug delivery processor 90. The display control processor 80 receives as further input from the drug delivery processor 90 the ESA drug dosage rate plus alert and alarm information. The display control processor 80 stores data for printing and, optionally, may provide real time data output via a RS-232 data port. In one of its primary functions, the display control processor 80 controls and formats the graphic display 100 to provide visual displays for the operator. An ESA trend display 102 and labelling for the soft keys 104 are driven by the display control processor 80. The display control processor 80 drives an audiotone generator 82 to warn of alert and alarm conditions. Optionally, the display control processor 80 provides a system clock fed to the data acquisition processor 70 and drug delivery processor 90 to synchronize operation. Finally, a system watch dog hardware circuit checks the display control processor 80 for proper operation.

The drug delivery processor 90 functions principally to determine the drug infusion rate as determined by the control method system. The drug delivery processor 90 receives alerts and alarms, plus heart rate and blood pressure data from the display control processor 80, plus inputs from the hard key pad 110. Additionally, the drug delivery processor 90 receives a response signal from the IV drug delivery source 120. Patient specific data is input from the hard key pad 110, which is optionally transmitted to the display control processor 80 for display. The hard key pad 110 provides the input for initial heart rate target and heart rate slope, patient specific data (such as weight and age) plus protocol adjustments such as changes to heart rate target, heart rate slope or the HOLD mode. The drug delivery processor 90 monitors the IV drug delivery pump 122 for alerts and verifies dose rate commands. The drug delivery processor 90 drives a second audiotone generator 92 to indicate one of alerts and alarm conditions. The drug delivery processor 90 also controls the system status LEDs 106. A second watchdog hardware circuit 94 checks the drug delivery processor for proper operation.

All of the rules described above are stored in memory for use by the various processors. Any form of memory, whether solid state, magnetic or otherwise, may be used to store the program and rules.

The IV drug delivery source 120 may consist of any drug delivery apparatus consistent with the invention. In one embodiment, an intravenous drug delivery system is used. A IV syringe pump 122 controls drug administration rate by controlling motion of a syringe plunger. Preferably, the syringe is contained under an interlocked cover. The IV extension set connects the syringe to venipuncture device, not shown. In operation, the IV drug delivery source 120 provides the drug delivery processor 90 with infusion rate information.

In an alternative embodiment, a transdermal drug delivery system may be utilized. The details of a particularly useful transdermal drug delivery system are described in Apparatus and Method for Iontophoretic Transfer, Serial No. 07/471,296, Filed Jan. 26, 1990, incorporated herein. Preferably, the drug delivery processor 90 would provide the transdermal dose commands to the transdermal drug delivery current source 130. The current source 130 then drives the drug electrode 132 with the indifferent electrode 134 providing the completion to the current circuit. Optionally, voltage and current confirmation may be provided from the transdermal drug delivery device to the drug delivery processor 90. Preferably, the transdermal drug delivery current course 130 limits the current and voltage to safe levels, such as voltage less than 100 volts dc max and current less than 5 milliamps.

Though the invention has been described with respect to a specific preferred embodiment, many variations and modifications will immediately become apparent to those skilled in the art. It is therefore the invention that the appended claims be interpreted as broadly as possible in view of the prior art to include all such variations and modifications.

We claim:

1. A method for varying a patient heart rate using an exercise simulating drug in a closed-loop drug delivery system wherein the system has a processor that controls the delivery of the drug to the patient, comprising the steps of:
    a) defining a protocol for implementation on the processor, the protocol including at least a target heart rate, a first plan to achieve the target heart rate, an alternate plan to achieve a second target heart rate, and transition conditions to cause the system to transition from the first plan to the alternate plan, where both first and alternate plans provide a non-zero amount of drug to the patient,
    b) beginning the drug delivery to initiate the protocol,
    c) monitoring the patient heart rate, wherein the monitored heart rate is received by the processor and
    d) modifying the protocol implemented on the processor from the first plan to the alternate plan after the drug delivery begins and when the processor determines that the monitored heart rate satisfies the transition conditions wherein the modification changes the rate of the drug delivery.

2. The method for control of a patient heart rate of claim 1 where in step d the protocol is modified by varying the target heart rate.

3. The method for control of a patient heart rate of claim 1 where in step a the protocol further includes defining the desired rate of increase in patient heart rate during closed-loop drug delivery.

4. The method of claim 3 where in step d the protocol is modified by varying the desired rate of increase in the patient heart rate.

5. A method for varying a patient physiological variable in a closed-loop drug delivery system wherein the system has a processor that controls the delivery of the drug to the patient, comprising the steps of:
    a) defining a protocol for implementation on the processor including a first target value of the patient physiological variable and a first set of rules to achieve the first target value of the patient physiological variable,
    b) defining an alternate set of rules to achieve a second target value of the patient physiological variable, where both the first and alternate sets of rules provide a non-zero amount of drug to the patient,
    c) defining an acceptable zone of deviation from the first set of rules,
    d) initiating drug delivery at a rate defined by the first set of rules,
    e) monitoring the patient physiological variable to generate a monitored value wherein the monitored value is received by the processor, and
    f) changing from the first set of rules to the alternate set of rules if the processor determines that the monitored value of the patient physiological variable is outside the acceptable zone of deviation from the first set of rules, thereby changing the rate of the drug delivery.

6. The method of claim 5 wherein the patient physiological variable is the heart rate.

7. The method of claim 5 or 6 where in step b the alternate set of rules include an alert or alarm condition.

8. The method of claim 5 or 6 where in step b the alternate set of rules includes open-loop administration of the drug.

9. The method of claim 5 or 6 where the alternate set of rules affects the administration of drug delivery and includes a proportional-integral control rule that has i) a proportionality error component proportional to the difference between the second target value and the monitored value of the physiological variable and ii) an integral error term that is an integral over time of the proportionality error component.

10. The method of claim 5 or 6 where in step b the alternate set of rules affects the administration of drug delivery and includes a proportional-integral-derivative control rule that has i) a proportionality error component that is proportional to the difference between the second target value and the monitored value of the physiological variable, ii) an integral over time of the proportionality error component, and iii) a derivative over time of the proportionality error component.

11. The method of claim 5 or 6 where in step c the acceptable zone of deviation from the first set of rules includes definition of a maximum acceptable value for the patient physiological variable.

12. The method of claim 5 or 6 where in step c the acceptable zone of deviation from the first set of rules includes a maximum acceptable rate of increase in the patient physiological variable.

13. The method of claim 5 or 6 where in step a the first set of rules affects the administration of drug delivery and includes a proportional-integral control rule that has: i) a proportionality error component proportional to the difference between the second target value and the monitored value of the physiological variable; and ii) an integral error term that is an integral over time of the proportionality error component.

14. The method of claims 5 or 6 where in step a the first set of rules affects the administration of drug delivery and includes a proportional-integral-derivative control rule that has i) a proportionality error component proportional to the difference between the second target value and the monitored value of the physiological variable, ii) an integral over time of the proportionality error component, and iii) a derivative over time of the proportionality error component.

15. A method for closed-loop drug delivery to a patient for varying a patient physiological variable, the method using a system wherein the system has a processor that controls the delivery of the drug to the patient, the method comprising the steps of:
    a) administering the drug to the patient,
    b) determining the individual patient response, including an onset delay, to the administered drug, wherein the onset delay is the interval between the time drug administration begins and a change in the patient physiological variable is measured, and
    c) adjusting the administration of the drug with closed-loop control of drug delivery wherein the processor adjusts drug delivery by utilizing the individual patient response information, including the onset delay, in the patient response to the drug.

16. The method of claim 15 where the individual patient response information includes the heart rate gain per unit drug infusion.

17. The method of claim 15 wherein step b further includes determining an estimation of a time constant for drug response for the patient.

18. The method of claim 15 wherein the drug is an exercise simulation agent.

19. A method for using closed-loop drug delivery to vary a patient physiological variable, the method using a system wherein the system has a processor that controls the delivery of the drug to the patient, the method comprising the steps of:
    a) specifying a first desired rate of change in the patient physiological variable, a second desired rate of change in the patient physiological variable, and transition conditions to indicate when to switch from the first desired rate of change to the second desired rate of change, where both the first and second desired rates of change provide a non-zero amount of drug to the patient,
    b) administering the drug which causes variation in the patient's physiological variable,
    c) monitoring the patient physiological variable wherein the monitored value is received by the processor,
    d) determining a determined rate of change in the patient physiological variable, and
    e) controlling the drug delivery in the closed-loop system whereby the determined rate of change in the patient physiological variable is adjusted by the processor toward the first desired rate of change in the patient physiological variable, and when the monitored patient physiological variable satisfies the transition conditions, the determined rate of change is adjusted by the processor toward the second desired rate of change of the patient physiological variable.

20. The method of claim 19 wherein the patient physiological variable is the heart rate.

21. The method of claim 19 wherein the desired rate of change in the patient physiological variable is a positive number.

22. A method for closed-loop drug delivery using an exercising simulating agent drug for adjusting a heart rate, the method using a system wherein the system has a processor that controls the delivery of the drug to the patient, the method comprising the steps of:
    a) specifying for implementation on the processor i) a first protocol that includes a first target heart rate, ii) an alternate protocol that includes a second target heart rate and, iii) transition conditions for indicating whether to switch from the first protocol to the second protocol,
    b) establishing a baseline heart rate approximately equal to the patient's average heart rate at the initial start of drug administration,
    c) determining the individual patient response to the drug, including, monitoring the heart rate to find a monitored heart rate, wherein the monitored heart rate is received by the processor,
    d) adjusting the administration of the drug based upon: i) the first protocol, or the second protocol when transition conditions are met, ii) the baseline heart rate, iii) the monitored heart rate, and iv) the individual patient response,
    e) collecting patient specific data about the patient response to the drug, and
    f) outputting the patient specific data about the patient response to the drug.

23. The method of claim 22 wherein the first protocol specifies the desired rate of increase in the heart rate.

24. The method of claim 22 wherein the first protocol specifies the time that the monitored heart rate is to be held at the target heart rate.

25. The method of claim 22 wherein the first protocol utilizes patient specific information to affect drug delivery.

26. The method of claim 22 further including the step of establishing a baseline blood pressure equal to the patient's average blood pressure at the initial start of drug administration.

27. The method of claim 22 where in step c, the individual patient response is determined in response to an open loop administration of the drug.

28. The method of claim 22 wherein step c, the determination of individual patient response includes the gain in the patient heart rate per unit drug infusion.

29. The method of claim 22 wherein step c the determination of individual patient response includes determination of the time required for the patient response to respond measurably to the drug.

30. The method of claim 22 wherein the monitored heart rate of step d uses an average of the monitored heart rates.

31. The method of claim 22 further including the step of monitoring the patient blood pressure and wherein the administering of the drug in step d is also adjusted based upon the monitored blood pressure.

32. The method of claim 22 further including the step of monitoring for saturation of the patient response to the drug wherein saturation occurs when the patient heart rate does not change sufficiently with drug administration.

33. The method of claim 22 where in step d the first protocol includes a ramp mode whereby increased administering of the drug causes the patient response to the drug to increase.

34. The method of claim 22 where in step d the first protocol includes an initialization mode whereby the first protocol is initialized to the patient's particular response to the drug.

35. The method of claim 22 where in step d the first protocol includes a level mode whereby the drug is administered such that the patient response to the drug is kept constant.

36. The method of claim 22 where in step d the first protocol affects the administration of drug delivery and includes a proportional-integral control rule that has a proportionality error component proportional to the difference between the second target value and the monitored value of the physiological variable and an integral error term that is an integral over time of the proportionality error component.

37. The method of claim 22 where in step e, the output includes a plot of trends in the patient response to the drug.

38. The method of claim 22 where in step e, the output includes real time data.

39. The method of claim 22 further including the step of issuing alerts or alarms if a hazardous or unexpected patient response to the drug is detected.

40. The method of claim 22 further including the step of filtering the monitored heart rate.

41. The method of claim 22 where in step d the first protocol includes a HOLD mode whereby the drug is administered such that the patient monitored heart rate is held at the target heart rate.

42. A method for achieving a HOLD mode in a closed-loop drug delivery system wherein the system has a processor that controls rates of drug delivery to a patient and where the rate of drug delivery affects a physiological parameter of the patient, comprising the steps of: setting a desired value for the physiological parameter, reducing initially the rate of drug delivery, increasing the rate of drug delivery, and measuring the physiological parameter wherein the measured physiological parameter is used by the processor to control the rate of drug delivery such that at the end of the increase, the rate of drug delivery results in maintenance of the physiological parameter at the desired value.

43. The reducing step of claim 42 wherein the initial reduction in the rate of drug delivery is to a zero rate of infusion.

44. The increasing step of claim 42 in which the rate of drug delivery is increased exponentially.

45. A method for detecting saturation in cardiac response to the drug delivery method of claim 1 further comprising the steps of:
monitoring for peak heart rate,
determining the length of time since the last heart rate peak was detected, and generating a signal indicative of the saturation when the length of time since the last heart rate peak was detected exceeds a pre-set time limit.

46. The method of claim 45 where in the pre-set time limit is 30 seconds.

47. The method of claim 19 for using closed-loop drug delivery to vary a patient physiological variable further comprising the steps:

f) comparing the determined rate of change with a threshold rate of change, and g) generating a signal indicative of a saturation condition if the determined rate of change is less than the threshold rate of change.

48. In a closed-loop drug delivery method implemented on a closed-loop control system having a processor, the method administering an exercising simulating agent to elicit stress, where the patient heart rate is monitored in response to the administration of the drug and the patient heart rate is used in the closed-loop control system to adjust the drug delivery, the improvement in the method comprising:

a) monitoring the drug administration and the patient heart rate for a saturation level of the drug wherein the monitored values are received by the processor and where the saturation level is reached when the processor determines that the patient heart rate changes insufficiently with drug administration, and b) adjusting the drug administration in response to the saturation level.

49. A method for determining when a target heart rate has been achieved in a closed-loop drug delivery system wherein the system has a processor that controls the delivery of the drug to the patient, comprising the steps of:

initiate drug delivery, monitor the patient heart rate wherein the monitored heart is received by the processor, determine the slope of the patient heart rate, generate a threshold to target value based in part on the heart rate slope, wherein the threshold to target value represents an acceptable deviation from the target heart rate, and terminate drug delivery when the processor determines that the patient heart rate exceeds the target heart rate minus the threshold to target value.

50. The method for determining when a target heart rate has been achieved in claim 49 where the threshold to target value is generated based upon the heart slope and desired heart rate slope.

51. The method for determining when a target heart rate has been achieved of claim 50 where the threshold to target value is generated based upon the average of the heart rate slope and the desired slope.

* * * * *